US011443846B2

(12) United States Patent
Schoenefeld et al.

(10) Patent No.: US 11,443,846 B2
(45) Date of Patent: Sep. 13, 2022

(54) INTEGRATED ORTHOPEDIC PLANNING AND MANAGEMENT PROCESS

(71) Applicant: Biomet Manufacturing Corp., Warsaw, IN (US)

(72) Inventors: Ryan John Schoenefeld, Fort Wayne, IN (US); Troy W. Hershberger, Winona Lake, IN (US); Bryan Morrison, Goshen, IN (US); Joshua B. Catanzarite, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 305 days.

(21) Appl. No.: 16/005,055

(22) Filed: Jun. 11, 2018

(65) Prior Publication Data

US 2018/0358120 A1 Dec. 13, 2018

Related U.S. Application Data

(63) Continuation of application No. 14/052,908, filed on Oct. 14, 2013, now abandoned, which is a (Continued)

(51) Int. Cl.
*A61B 34/10* (2016.01)
*G06T 13/40* (2011.01)
(Continued)

(52) U.S. Cl.
CPC .............. *G16H 30/40* (2018.01); *A61B 34/10* (2016.02); *G16H 15/00* (2018.01); *G16H 20/40* (2018.01);
(Continued)

(58) Field of Classification Search
CPC ........ G16H 50/50; G16H 80/00; G16H 30/40; G16H 15/00; G16H 20/40; A61B 34/10;
(Continued)

(56) References Cited

U.S. PATENT DOCUMENTS

| 5,880,976 A | 3/1999 | DiGioia III et al. |
| 6,205,411 B1 | 3/2001 | Digioia, III et al. |

(Continued)

FOREIGN PATENT DOCUMENTS

| EP | 2644156 A1 | 10/2013 |
| WO | WO-2013052187 A | 4/2013 |

OTHER PUBLICATIONS

"U.S. Appl. No. 13/910,188, Final Office Action dated Feb. 5, 2015", 31 pgs.

(Continued)

*Primary Examiner* — Maroun P Kanaan
(74) *Attorney, Agent, or Firm* — Schwegman Lundberg & Woessner, P.A.

(57) ABSTRACT

A method can include receiving, at a server, preoperative image data of a patient's bone, and accessing, at the server, a database of three-dimensional model data. A patient specific three-dimensional model of the patient's bone can be generated, at the server. A preoperative surgical plan can be generated at the server, which can include comparing aspects of the preoperative surgical plan with predetermined reliability criteria. An interactive user interface for use by a surgeon to review the preoperative surgical plan can be provided, from the server, to a user device. Approval of the preoperative surgical plan can be received, at the server, via the interactive user interface. Postoperative image data of the patient's bone can be received at the server. A postoperative outcome study report can be generated, at the server, and can include a comparison of the preoperative surgical plan with the postoperative image data.

21 Claims, 16 Drawing Sheets

Related U.S. Application Data continuation-in-part of application No. 13/910,188, filed on Jun. 5, 2013, now abandoned.

(60) Provisional application No. 61/808,879, filed on Apr. 5, 2013.

(51) Int. Cl.
  *G16H 30/40* (2018.01)
  *G16H 15/00* (2018.01)
  *G16H 20/40* (2018.01)
  *G16H 50/50* (2018.01)

(52) U.S. Cl.
  CPC ........ *G16H 50/50* (2018.01); *A61B 2034/102* (2016.02)

(58) Field of Classification Search
  CPC ........ A61B 2034/105; A61B 2034/108; A61B 90/37; A61B 2034/102; G06F 19/00; G06F 19/3418; G06F 19/3481; G06F 30/00; G06F 19/321; G06F 3/011; G06F 3/016
  See application file for complete search history.

(56) References Cited

U.S. PATENT DOCUMENTS

| | | | |
|---|---|---|---|
| 6,514,259 | B2 | 2/2003 | Picard et al. |
| 2004/0030245 | A1 | 2/2004 | Noble et al. |
| 2007/0173815 | A1* | 7/2007 | Murase ............ G16H 50/50 606/53 |
| 2008/0009697 | A1 | 1/2008 | Haider et al. |
| 2008/0077158 | A1 | 3/2008 | Haider et al. |
| 2009/0171184 | A1 | 7/2009 | Jenkins et al. |
| 2009/0234217 | A1* | 9/2009 | Mire ............ A61B 34/20 600/407 |
| 2009/0243833 | A1 | 10/2009 | Huang et al. |
| 2011/0092804 | A1 | 4/2011 | Schoenefeld et al. |
| 2012/0020540 | A1 | 1/2012 | Aghazadeh |
| 2012/0123418 | A1 | 5/2012 | Giurgi et al. |
| 2012/0130687 | A1 | 5/2012 | Otto et al. |
| 2012/0274631 | A1 | 11/2012 | Friedland et al. |
| 2013/0066647 | A1 | 3/2013 | Andrie et al. |
| 2013/0085590 | A1 | 4/2013 | Bryan et al. |
| 2013/0261503 | A1 | 10/2013 | Sherman |
| 2013/0307955 | A1 | 11/2013 | Deitz et al. |
| 2014/0081659 | A1 | 3/2014 | Nawana et al. |
| 2014/0303938 | A1 | 10/2014 | Schoenefeld et al. |
| 2014/0303990 | A1 | 10/2014 | Schoenefeld et al. |
| 2016/0045317 | A1* | 2/2016 | Lang ............ G05B 19/4099 700/98 |

OTHER PUBLICATIONS

"U.S. Appl. No. 13/910,188, Non Final Office Action dated Aug. 15, 2014", 29 pgs.

"U.S. Appl. No. 13/910,188, Response filed Nov. 12, 2014 to Non Final Office Action dated Aug. 15, 2014", 14 pgs.

"U.S. Appl. No. 14/052,908, Advisory Action dated Apr. 26, 2017", 6 pgs.

"U.S. Appl. No. 14/052,908, Final Office Action dated Jan. 31, 2017", 47 pgs.

"U.S. Appl. No. 14/052,908, Final Office Action dated Mar. 9, 2018", 52 pgs.

"U.S. Appl. No. 14/052,908, Non Final Office Action dated Jun. 6, 2016", 43 pgs.

"U.S. Appl. No. 14/052,908, Non Final Office Action dated Aug. 10, 2017", 49 pgs.

"U.S. Appl. No. 14/052,908, Response filed Mar. 31, 2017 to Final office Action dated Jan. 31, 2017", 14 pgs.

"U.S. Appl. No. 14/052,908, Response filed Apr. 27, 2017 to Advisory Action dated Apr. 26, 2017", 14 pgs.

"U.S. Appl. No. 14/052,908, Response filed Oct. 5, 2016 to Non Final Office Action dated Jun. 6, 2016", 12 pgs.

"U.S. Appl. No. 14/052,908, Response filed Nov. 10, 2017 to Non Final Office Action dated Aug. 10, 2017", 16 pgs.

Metzger, Marc Christian, et al., "Verification of clinical precision after computer-aided reconstruction in craniomaxillofacial surgery", Oral Surgery, Oral Medicine, Oral Pathology, Oral Radiology, and Endodontology 104.4, (2007).

* cited by examiner

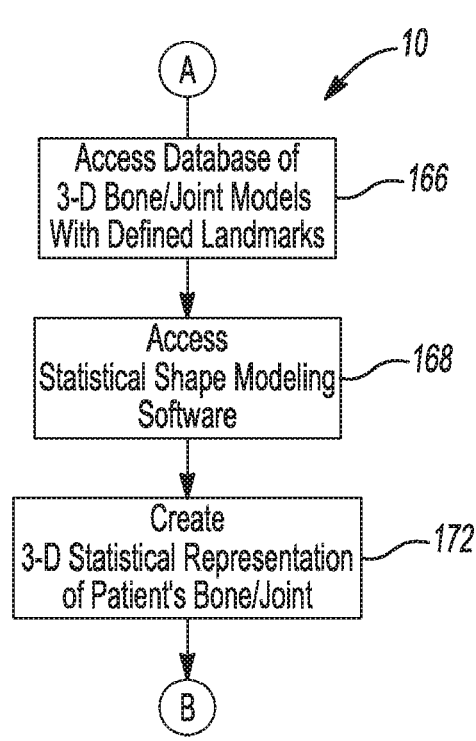
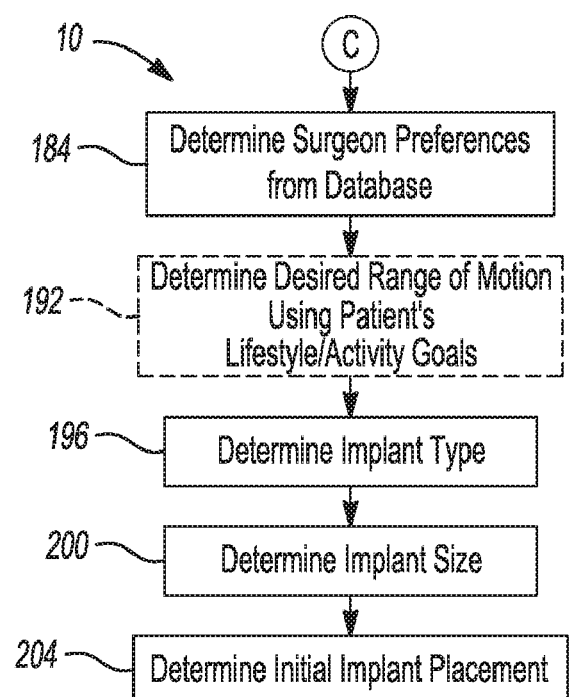
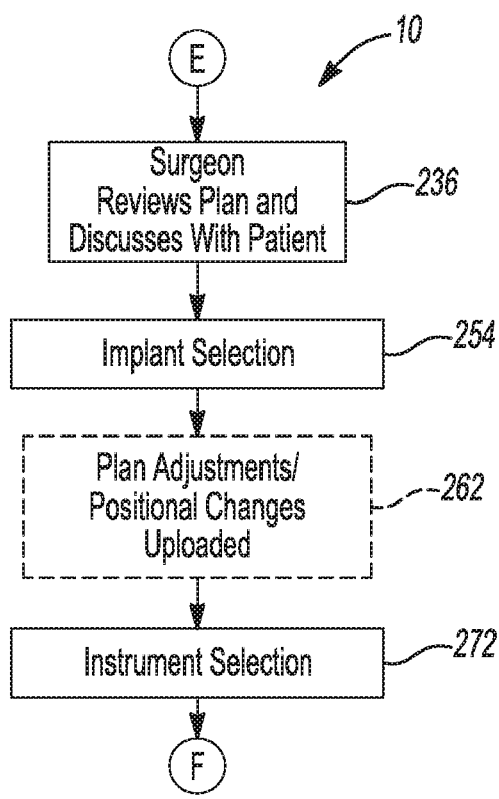
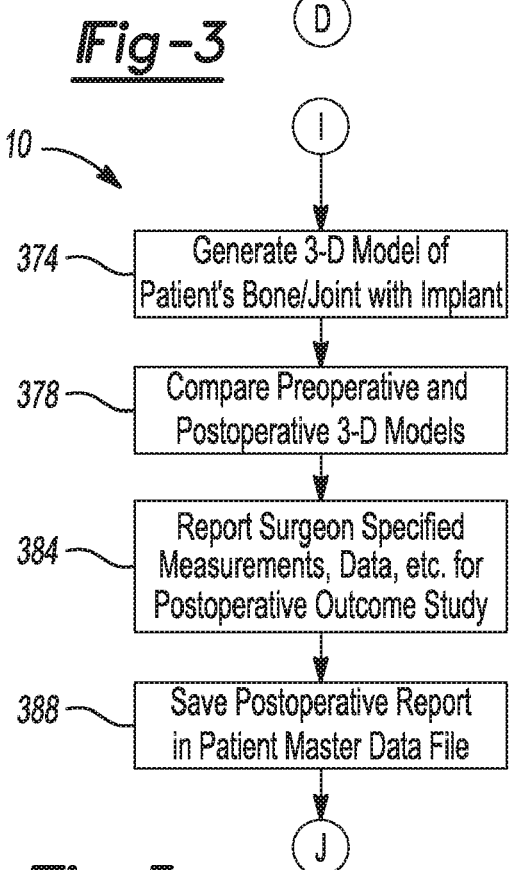

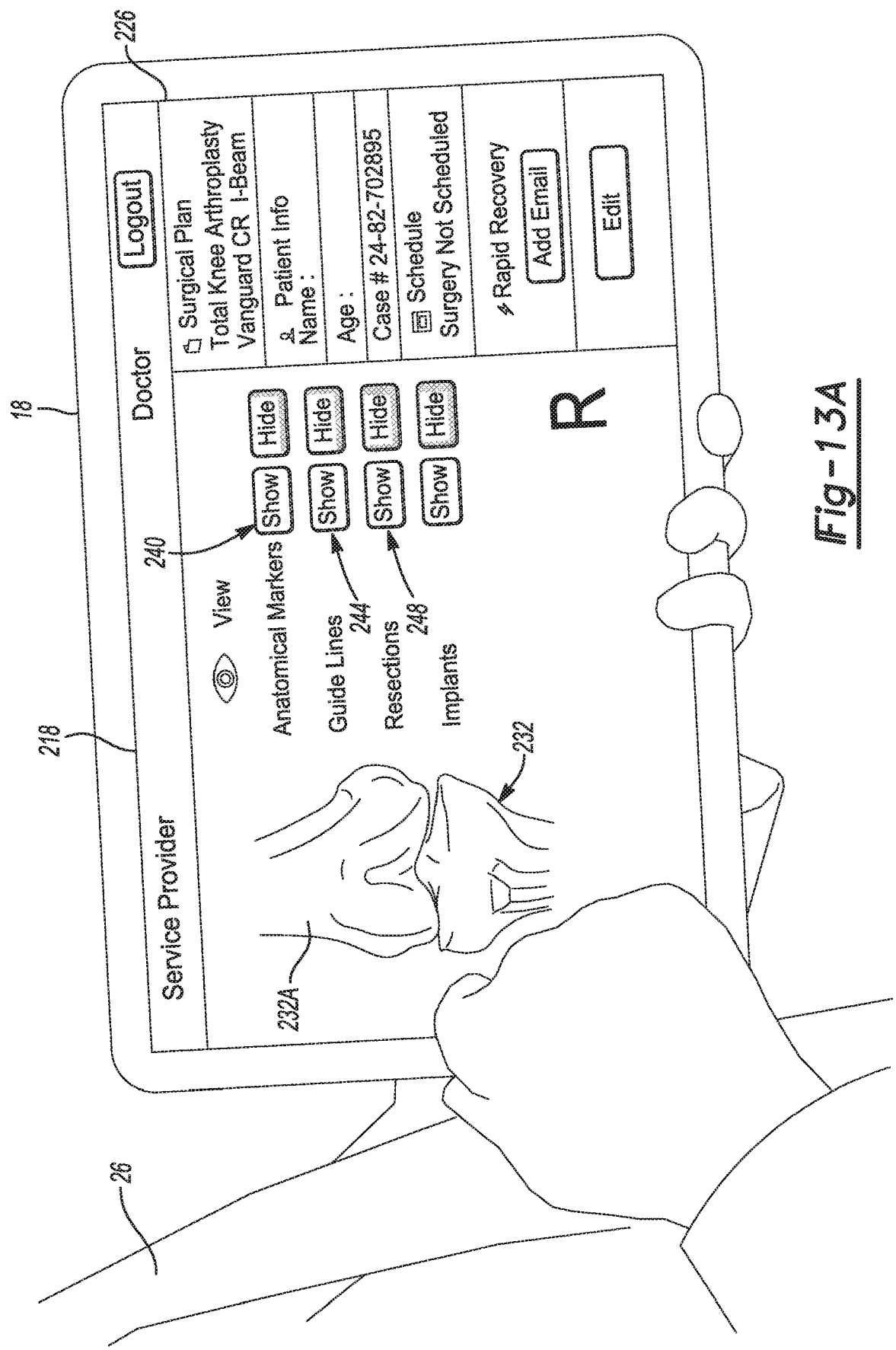

Service Provider

Patient Info
Name:
Age:
Case # 24-82-702895

Instrument Summary
Vanguard Premier Kit
(CR-62.5) (I-Beam-71)
X Tibial Trials
X Alignment Guides Vanguard Select Disposable
Tibial Trials
Alignment Guides

Doctor | Logout

| Tibia | Finned | Femur | Vanguard CR |
|---|---|---|---|
| Varus (+) Valgus (−) | 0.0 DEG | Varus (+) Valgus (−) | 0.0 DEG |
| Resection From Highest Point | 10.0 MM | Medial Distal Resection | 10.5 MM |
| Posterior Slope | 3.0 DEG | Size | 6.25 |
| Size | 71 | Flexion (+) Extension (−) | 3.0 DEG |
| Rotation | 0.0 MM | Medial Posterior Resection | 9.5 MM |
| | | Rotation From Epicondylar | 0.0 MM |

Surgical Time 00:10:42

R

Logout

*Fig-16B*

INTEGRATED ORTHOPEDIC PLANNING AND MANAGEMENT PROCESS

CROSS-REFERENCE TO RELATED APPLICATIONS

This application claims the benefit of U.S. Provisional Application No. 61/808,879, filed on Apr. 5, 2013, and U.S. application Ser. No. 13/910,188, filed on Jun. 5, 2013. The disclosure of the above applications is incorporated herein by reference.

FIELD

The present disclosure relates generally to a method for surgical planning and, more particularly, to a method for integrated orthopedic planning and management.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In general, an injured or defective bone or joint of a patient can be treated by a surgeon making intraoperative decisions during a surgery. Preoperative surgical planning can allow a surgeon to make certain surgical decisions or recommendations prior to performing the surgery. For example, the preoperative planning can include which implants and surgical devices are planned for use to repair the defective bone or joint. The capability for the surgeon to analyze images of the patient's defective bone or joint prior to surgery can allow the surgeon to develop a plan for conducting the actual surgery.

SUMMARY

This section provides a general summary of the disclosure, and is not a comprehensive disclosure of its full scope or all of its features.

In one form, a method for orthopedic planning and management is provided in accordance with various aspects of the present disclosure. The method can include receiving, at a server, preoperative image data of a patient's bone, and generating, at the server, a patient specific three-dimensional model of the patient's bone. A preoperative surgical plan based at least on the patient specific three-dimensional model can be generated at the server, which can include comparing aspects of the preoperative surgical plan with predetermined reliability criteria. An interactive user interface for use by a surgeon or delegated team member can be provided, from the server, to a user device, and can display the preoperative surgical plan. Approval of the preoperative surgical plan can be received, at the server, via the interactive user interface. Postoperative image data of the patient's bone joint can be received, at the server, and can include an image of an implant associated with the patient's bone. A postoperative outcome study report can be generated, at the server, and can include a comparison of the preoperative surgical plan with the postoperative image data.

In another form, a method for orthopedic planning and management is provided in accordance with various aspects of the present disclosure. The method can include receiving, at a server, preoperative two-dimensional image data of a patient's bone joint, and accessing, at the server, a database of three-dimensional model data of one or more bones of a type associated with the patient's bone joint, where the three-dimensional bone data can include defined anatomical landmarks for use for surgical planning. A patient specific three-dimensional model of the patient's bone joint can be generated automatically, at the server, and can include identification of anatomical landmarks based at least on the preoperative image data and the database three-dimensional model data. A preoperative surgical plan can be generated, at the server, based at least on the patient specific three-dimensional model, and can include: comparing aspects of the preoperative surgical plan with predetermined reliability criteria and determining whether the preoperative surgical plan meets the predetermined reliability criteria; providing, from the server upon determining that the preoperative plan does not meet the predetermined reliability criteria, a notification to a predetermined user device; and receiving, at the server, input responsive to the notification. An interactive user interface for use by a surgeon or delegated team member can be provided automatically, from the server, to a user device, and can display the preoperative surgical plan. Input from the interactive user interface indicating contents of a patient specific surgical kit order for use with the patient can be received, at the server, where the kit can include one or more of (i) an implant, (ii) instrumentation, (iii) one or more guides, and (iv) a trial. Approval of the preoperative surgical plan can be received, at the server, via the interactive user interface. Information regarding the contents of the ordered patient specific kit can be provided, from the server, to a system or user device of an assembler of the ordered patient specific kit. Postoperative image data of the patient's bone joint can be received, at the server, and can include images of implants associated with the patient's bone joint. A postoperative outcome study report can be generated, at the server, and can include a comparison of the preoperative surgical plan with the postoperative image data. The postoperative outcome study report can be provided, from the server, to a user device associated with one or more of the surgeon, a medical facility and a regulatory body.

According to additional features, generating the patient specific three-dimensional model of the patient's bone joint can include accessing, at the server, statistical shape modeling software. The statistical shape modeling software can generate the three-dimensional model of the patient's bone joint based at least on the preoperative image data and an analysis of the database three-dimensional model data. In one exemplary implementation, a physical model can be generated from the patient specific three-dimensional model and the physical model can be provided to the surgeon or the medical facility.

In additional features, the database of three-dimensional model data can include defined anatomical landmarks for surgical planning. Generating the patient specific three-dimensional model of the patient's bone joint can include automatically identifying anatomical landmarks on the generated patient specific three-dimensional model based at least on the preoperative image data and the defined anatomical landmarks in the database three-dimensional bone model data.

In some examples, the interactive user interface for use by the surgeon or delegated team member can include (i) an implant selection portion, (ii) an instrument selection portion, and (iii) a guide selection portion. In some implementations, the interactive user interface can include information or applications or selection options regarding surgical navigation, sensor based technologies, and preoperative surgical plans, including implantation settings. In some implementations, the surgeon can select an option for creation of a custom implant.

According to additional features, data files for instrumentation to be utilized with the surgery can be provided, from the server to a user device. The data files can be utilized for manufacturing disposable instruments for use during the surgery and/or to be included in the patient specific kit. In one exemplary implementation, the instruments can be manufactured using rapid prototyping techniques. In another exemplary implementation, the patient specific kit can be assembled by a third party different from the manufacturer.

In other examples, a request for a user interface displaying preoperative preparation information can be received from a user interacting with a patient user device. A request for a user interface displaying selection options for patient specific recovery and education materials from a patient user interacting with a patient user device can also be received at the server. A patient specific user interface can be generated, at the server, and can include selection options for one or more of the following: (i) information about the patient's bone joint; (ii) information about the implants associated with the preoperative plan; (iii) information about the surgical procedure; (iv) preoperative preparation information; and (v) information about recovery (e.g., patient specific recovery and education materials). It should be appreciated that, in some implementations, one or more user interfaces can be generated having one or more of the above selection options.

In accordance with additional features, input to a patient satisfaction survey can be received at the server. Information from the patient satisfaction survey can be stored at a data store associated with the server. In one exemplary implementation, the postoperative outcome study report can include information from the patient satisfaction survey.

In some examples, a request can be received, at the server, to display the preoperative surgical plan at a user device in an operating room. An interactive user interface can be generated, at the server, and can be provided, from the server, for displaying at the operating room user device the preoperative surgical plan. Intraoperative data can be received, at the server, via the interactive user interface displayed at the operation room user device. In one exemplary implementation, an information tag associated with the patient specific kit or the contents thereof can be scanned prior to or during surgery. In this implementation, generating the interactive user interface for displaying the preoperative surgical plan in the operating room can occur automatically upon scanning the information tag.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 2 is a flowchart of a model generation portion of the process shown in FIG. 1 according to an aspect of the present disclosure;

FIG. 3 is a flowchart of a preoperative surgical plan generation portion of the process shown in FIG. 1 according to an aspect of the present disclosure;

FIG. 4 is a flowchart of a preoperative surgical plan review portion of the process shown in FIG. 1 according to an aspect of the present disclosure;

FIG. 5 is a flowchart of a postoperative report generation portion of the process shown in FIG. 1A according to an aspect of the present disclosure;

FIG. 13A is a view of an exemplary display or user interface illustrating an aspect of a preoperative surgical plan for review with a patient according to an aspect of the present disclosure;

FIG. 16B is an enlarged view of the display at the user or client device of FIG. 16A according to an aspect of the present disclosure.

DETAILED DESCRIPTION

Figure 1:
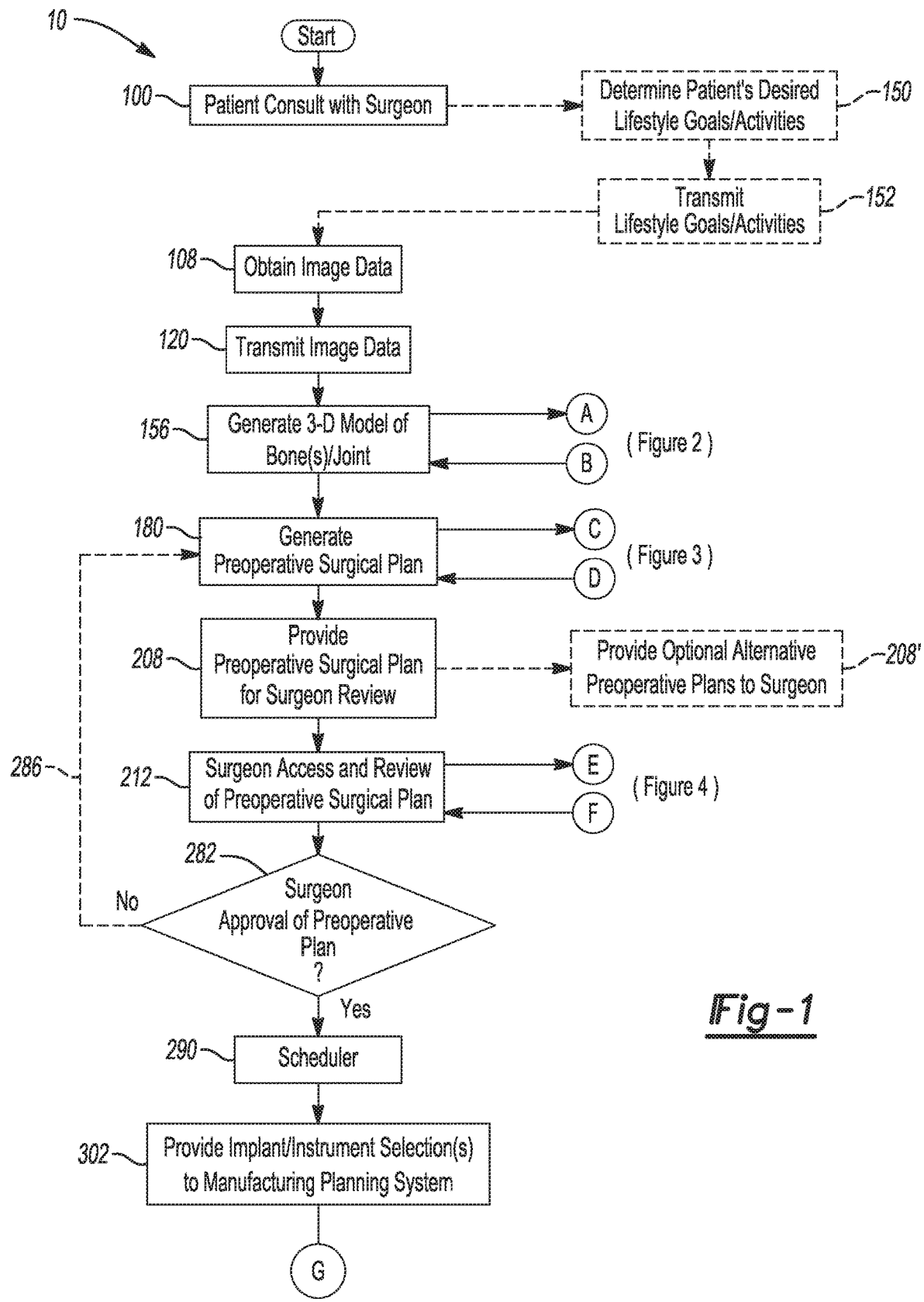
FIG. 1 is a flowchart of an exemplary digitally integrated orthopedic process in accordance with an aspect of the present disclosure.

The following description is merely exemplary in nature and is not intended to limit the present disclosure, its application, or uses. Although the following description is related generally to methods and systems for orthopedic planning and management with reference to a knee joint, it should be appreciated that the methods and systems discussed herein can be applicable to other bones and/or joints of the anatomy and/or any orthopedic implant.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide, in one exemplary implementation, a surgical planning and management process that integrates patient's anatomic and medical information with interactive participation by a surgeon, various hospital and/or imaging center personnel, and a service provider or original equipment manufacturer to plan and manage a surgery from initial consultation with a surgeon through postoperative reporting and archiving. In one exemplary implementation, the planning and management process includes a digitally integrated partially automated process utilizing a centralized user interface or web portal where the surgeon, hospital/imaging center personnel, original equipment manufacturer and patient can interact. The web portal can, in one exemplary implementation, provide various levels of user (e.g., surgeon, service provider and patient) access to various tools for case management, preoperative planning, communicating/sharing, manufacturing, surgical execution, and postoperative planning and data archiving.

The integrated process can provide a single source of access and information sharing thereby reducing complexity and increasing efficiency for the surgeon, hospital and original equipment manufacturer. As will be explained in more detail below by way of example, the web portal can facilitate a single source of access to an integrated workflow of tools and solutions guiding users through the preoperative planning, surgical execution and postoperative aspects of a surgery.

With initial reference to FIGS. 1-1A and 6-9, an exemplary integrated orthopedic planning and management process for an exemplary knee joint surgery is shown and generally identified at reference numeral 10. In general, the process 10 illustrates one example of a workflow between a patient, surgeon and manufacturer to plan and manage a surgery, including selection of an optimal implant and, in certain scenarios, various different instrumentation options. For example, a custom made implant specific to the patient, an implant that is only partially custom-made or a semi-custom implant, and a standard off—the shelf implant can be planned for the surgery. Similarly, off-the-shelf, custom-made, or semi-custom-made instrumentation (e.g. alignment guides, drill guides, cutting guides or other instruments) can be selected and manufactured, as approved by the surgeon, for the surgical procedure. All the implant components, alignment guides, and other reusable or disposable instruments can be included in a package or kit provided to a surgeon for a specific patient. As will be discussed herein, the integrated process 10 can facilitate more efficient delivery and reduce potential waste associated with surgical kits through improved information sharing and planning.

While the discussion of integrated process 10 will continue with reference to a knee joint surgery, it should be appreciated that the integrated process 10 can be applicable to various bone and/or joint related surgeries. Moreover, while process 10 illustrates various steps from initial surgeon consultation though postoperative reporting, it should also be appreciated that various different sub-portions of process 10 may be implemented or utilized by a surgeon depending on, for example, patient conditions and/or surgeon preferences.

Figure 6:
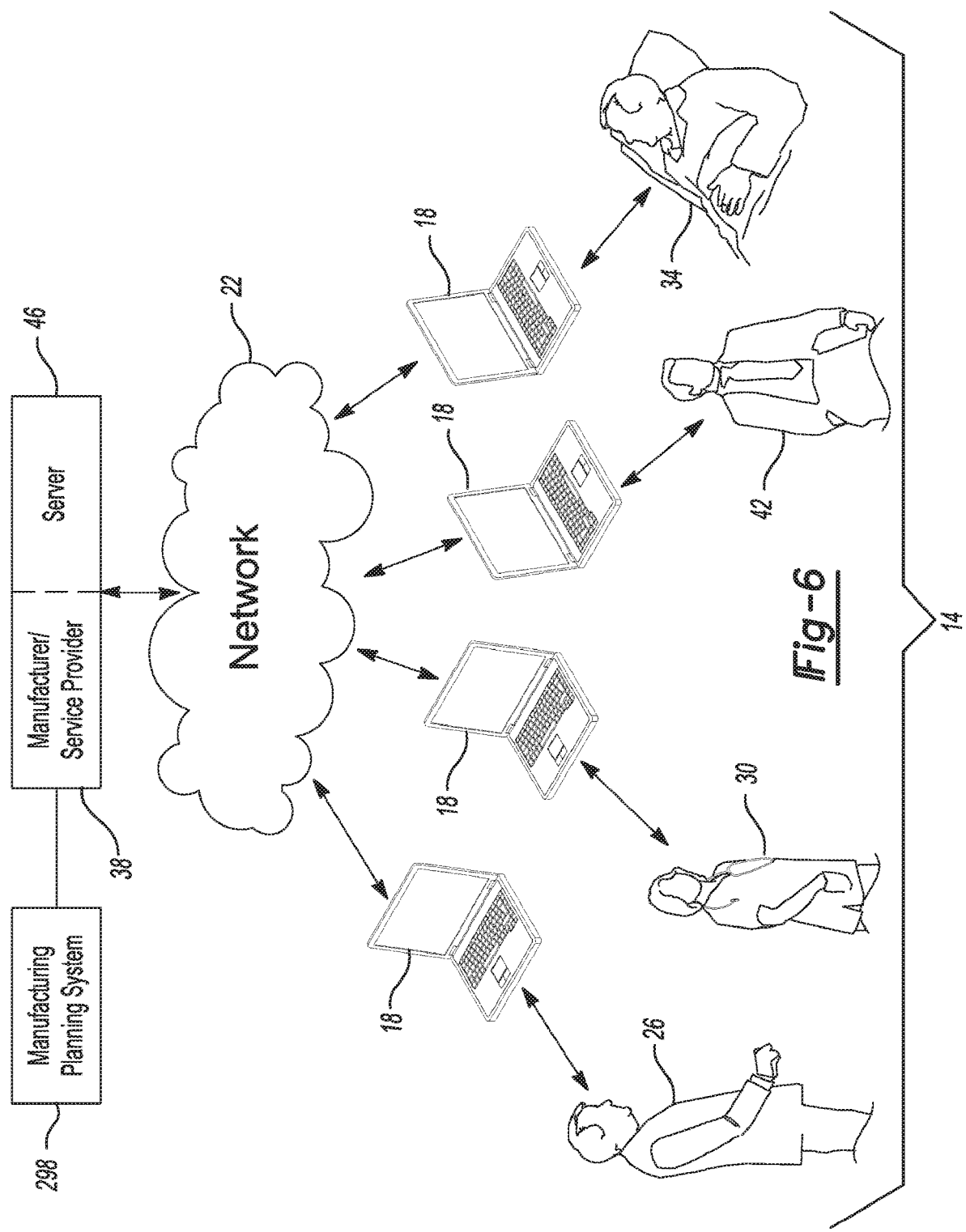
FIG. 6 is a schematic diagram of an exemplary server and an exemplary environment in which techniques according to an aspect of the present disclosure can be utilized.

FIG. 6 schematically illustrates an environment in which the process 10 can be utilized according to various aspects of the present disclosure. As shown in FIG. 6, various users 14 can interact via user devices 18 to access a network 22. In the particular environment illustrated, the users 14 can include a surgeon 26, imaging personnel 30, a patient 34, an original equipment manufacturer and/or service provider 38, and scheduling or other hospital personnel 42. It should be appreciated that the number of users can be more or less, and can include, for example, other hospital staff associated with surgical scheduling, etc. Examples of the network can include the Internet, a wide area network, a local area network, and a private network. The user devices 18 can be any appropriate user device including, but not limited to, a desktop computing device, a portable computing device, a handheld mobile device, a tablet, etc.

A computing device or server 46 can be connected to the network 22 and can be accessed by the various users 14 via user devices 18. In this regard, it should be appreciated that different users 14 can access the server 46 via different networks 22. For example, the surgeon 26 may access the server 46 via the Internet and the original equipment manufacturer 38 may access the server 46 via the local area network or private network. In the exemplary implementation illustrated in FIG. 6, the server 46 can be hosted by the original equipment manufacturer 38. It should be appreciated, however, that the server 46 could alternatively be hosted by a separate service provider. It should also be appreciated that while the present disclosure references a single computing device or server 46, the term "server" as used herein is meant to include both a single computing device or server as well as a plurality of computing devices or servers working in conjunction to perform the described techniques. For example only, the present disclosure may be implemented such that one or more servers 46 operate in conjunction with each other via a network to perform the described techniques, where each of the servers 46 can perform a portion of the described techniques.

Figure 7:
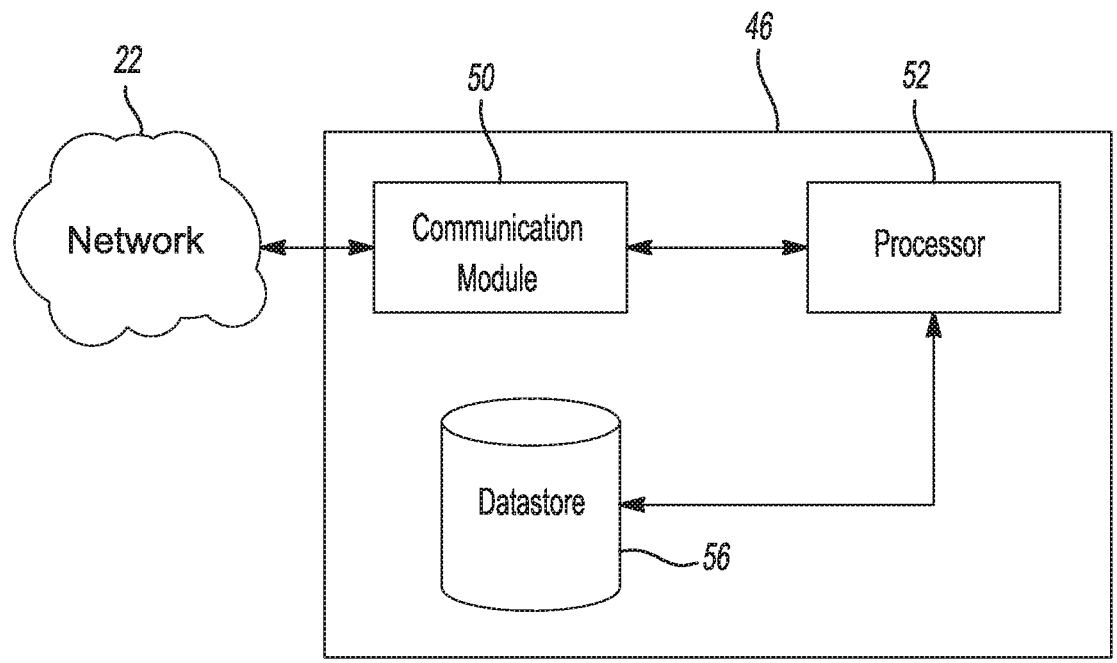
FIG. 7 is a schematic block diagram of the exemplary server of FIG. 6 according to an aspect of the present disclosure.
Figure 8:
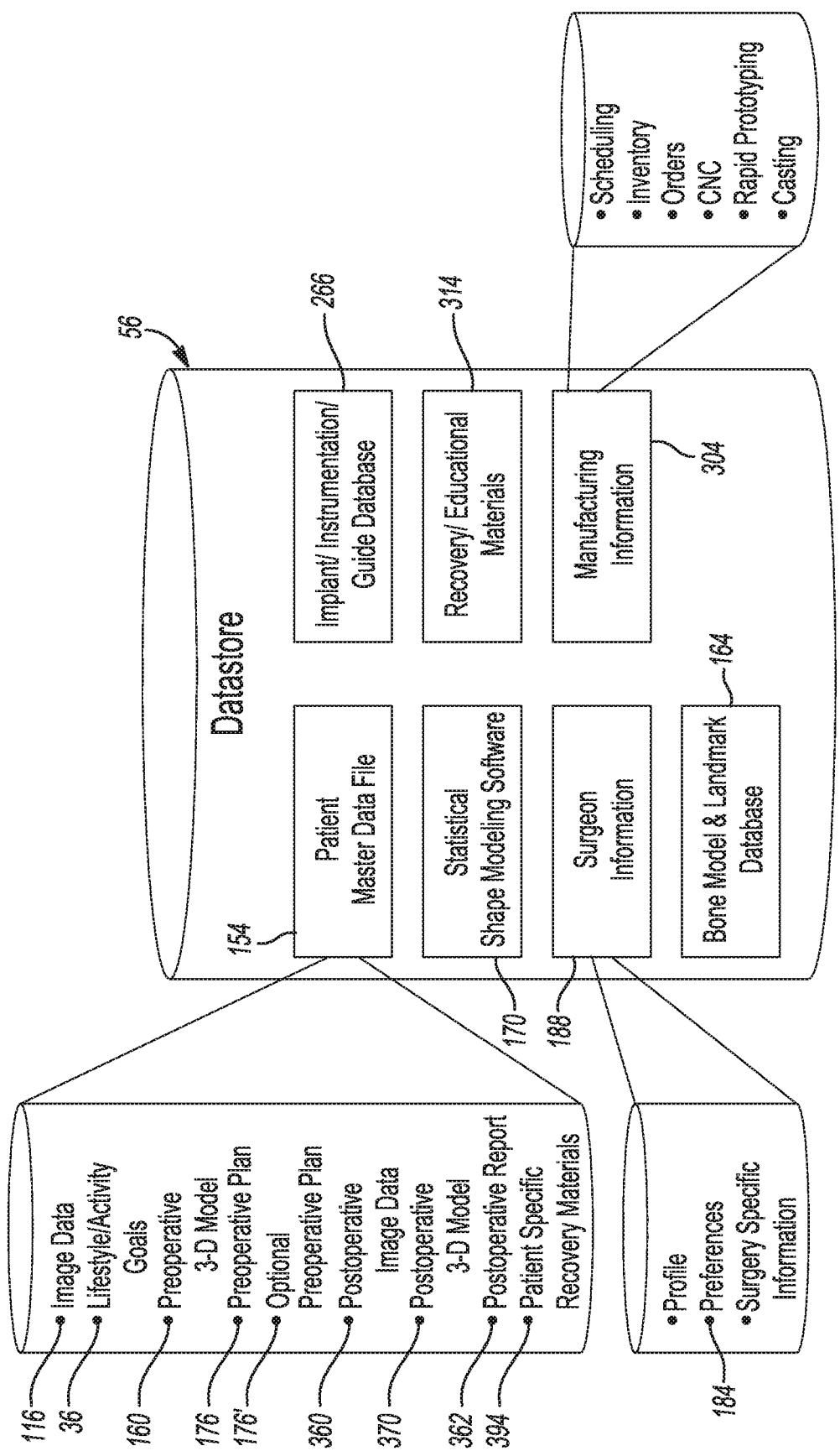
FIG. 8 is a schematic block diagram of an exemplary datastore of the exemplary server of FIG. 7 according to an aspect of the present disclosure.
Figure 10:
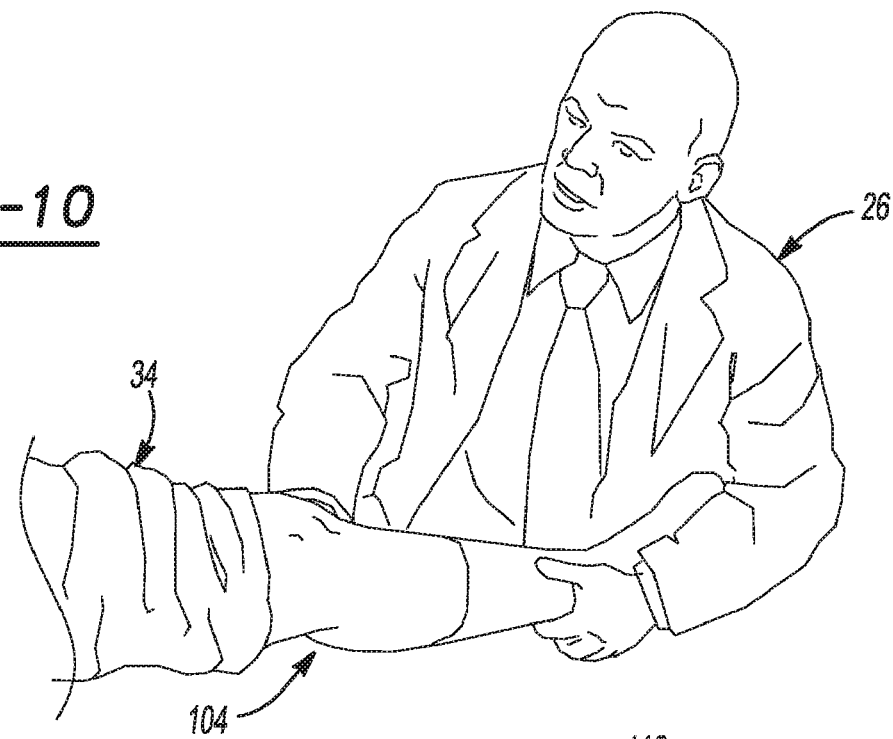
FIG. 10 is an exemplary illustration of a surgeon examining a patient for knee joint arthroplasty according to an aspect of the present disclosure.
Figure 11:
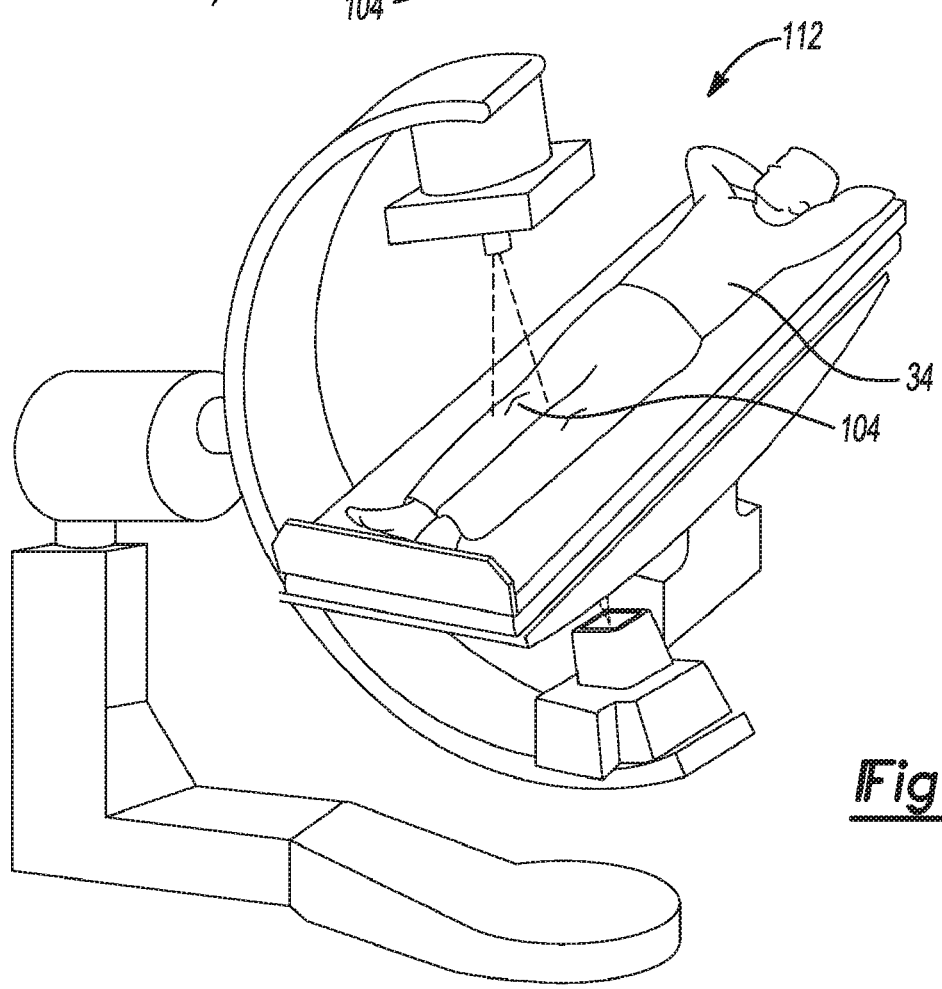
FIG. 11 is an exemplary illustration of the patient in preparation for the knee joint arthroplasty according to an aspect of the present disclosure.
Figure 12A:
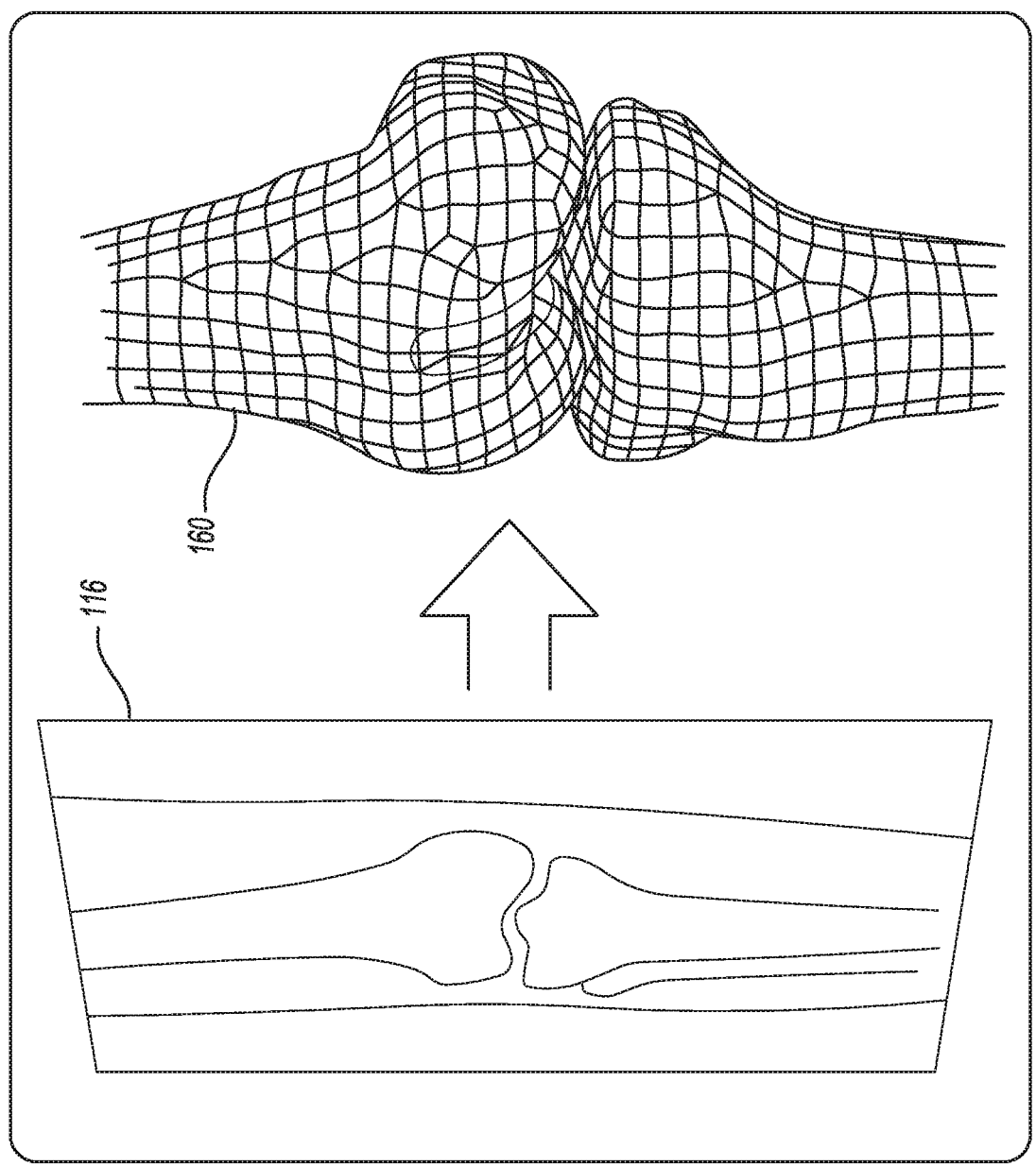
FIG. 12A is an exemplary view of image data acquired from the preparation associated with FIG. 11 and an illustration of an exemplary 3-D model of the patient's knee joint according to an aspect of the present disclosure.
Figure 12B:
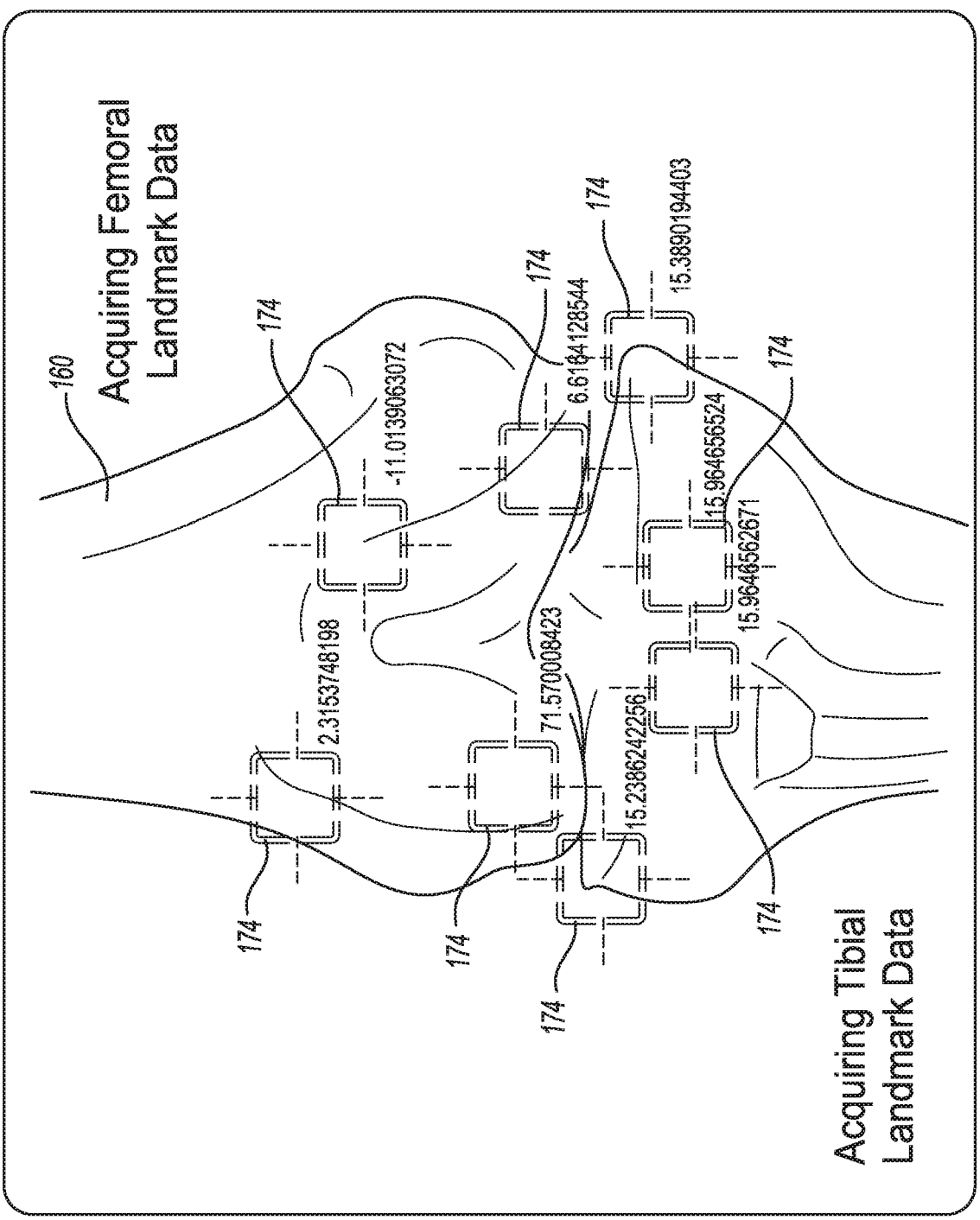
FIG. 12B is an exemplary illustration of a view of the 3-D model of FIG. 12A depicting an analysis of anatomical landmarks according to an aspect of the present disclosure.

A block diagram of the exemplary server 46 is illustrated in FIG. 7. The server 46 can include a communication module 50 in communication with a processor 52 and a memory or datastore 56. As shown in FIG. 8 and will be discussed in greater detail herein, the datastore 56 may store various types of information including software, data, programs, databases, etc. It should be appreciated that while a single datastore 56 is shown, the datastore 56 may be a collection of different types of storage. Similarly, the processor 52 may be a single processor or two or more processors operating in a parallel or distributed architecture.

Figure 9:
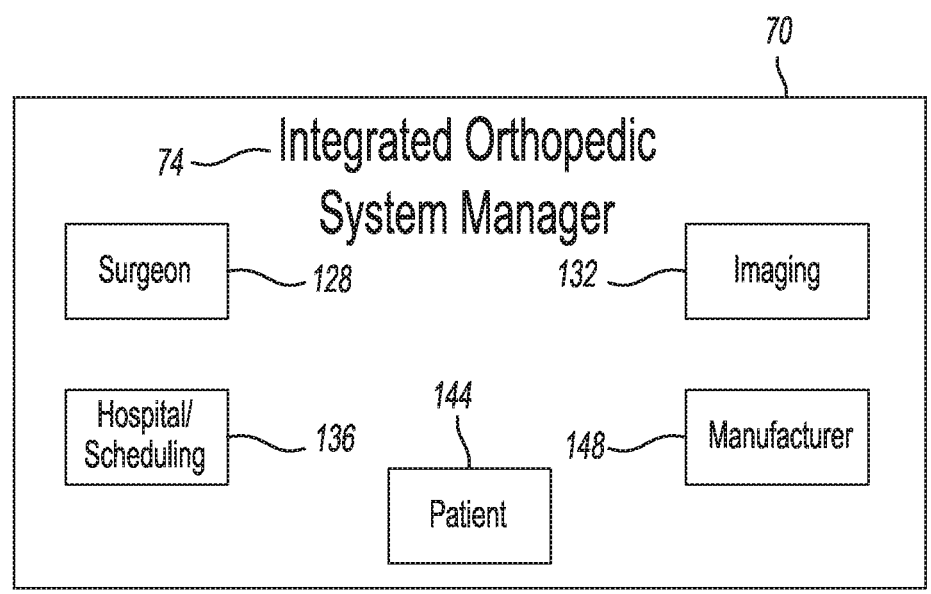
FIG. 9 is a representation of an exemplary web portal or user interface according to an aspect of the present disclosure.

Turning now to FIG. 9, an exemplary web portal or user interface 70 to a computer program for operation and management of the process 10 is illustrated schematically. An integrated orthopedic system manager 74 can be in the form of software, an operating system, or other computer program associated with the server 46 of the original equipment manufacturer 38. The integrated orthopedic system manager 74 can be accessible locally or remotely via user devices 18 and network 22, and can facilitate the process 10 as discussed herein.

With reference back to FIGS. 1-5 and additional reference to FIGS. 9-16B, the integrated orthopedic planning and management process 10 will now be discussed in greater detail. At block 100, the patient 34 can consult with a surgeon, such as the orthopedic surgeon 26, to address pain or discomfort in their knee joint 104, as shown in FIG. 1 with reference to FIG. 10. At block 108, the surgeon 26 can order image data, such as an X-ray 112 (FIG. 11) of the patient's knee joint 104. The X-ray data 116 (FIG. 12A) for the patient 34 can be obtained at a medical imaging facility or a doctor's office by the imaging personnel 30 and can be sent to the manufacturer 38 in an electronic and/or digital form.

In one exemplary implementation, the imaging personnel 30 can access the integrated orthopedic system manager 74 via the network 22 and user device 18 to transmit the X-ray data 116 to server 46 at block 120. In an exemplary implementation, the imaging personnel 30 can access the integrated orthopedic system manager 74 via a browser on the user device 18. The integrated orthopedic system manager 74 can then cause the user device 18 to display a user interface in the form of a web portal or login page 70, an example of which is schematically illustrated in FIG. 9.

It should be appreciated that the user interface 70 can be displayed in various forms and can include one or more login or access areas for various users, including an access area 128 for the surgeon 26, an access area 132 for the imaging personnel 30, an access area 136 for hospital/scheduling personnel 140, an access area 144 for the patient 34, and an access area 148 for the manufacturer 38.

It should also be appreciated that the various access areas 132-148 could be provided on the same or different user interfaces or, alternatively, the various users 14 could be provided with specific access criteria to directly access the integrated orthopedic system manager 74. For example, one or more of the user devices 18 can have installed programs that can be used to directly access user relevant aspects of the integrated orthopedic system manager 74 via web portal or user interface 70. Alternatively, or in addition thereto, the user devices 18 can access the server 46 that processes data files while receiving input through the user devices 18 and displaying images to the user 14 via the user device 18.

Upon accessing the integrated orthopedic system manager 74, the imaging personnel can transmit the X-ray data 116 to server 46. This information can be stored in datastore 56. A patient master data file 154 (FIG. 8) can be created and stored in datastore 56. In an alternative implementation, the imaging center/personnel 30 can have installed programs that automatically upload the X-ray data 116 to server 46.

Using 2-D X-ray data 116 (FIG. 12A) in connection with 3-D modeling (discussed below in greater detail) can leverage the use of lower-cost universal X-ray infrastructure thereby reducing costs. However, it should be appreciated that other forms of imaging and image data could be utilized, including photographs, MRI, CT, ultrasound, radiography, point cloud image data, or high resolution cameras, T-ray computed tomography and T-ray diffraction tomography. Digital photography can be useful in emergency situations, such as a trauma situation where there are potential constraints that prohibit obtaining X-ray or other image data. In such situations, the image data could be in the form of a digital photograph and the integrated orthopedic system manager 74 can be configured to automatically generate a preoperative surgical plan 176 tailored to such a trauma scenario.

Alternatively, a 3-D model of the bone and/or bone joint prepared by the surgeon 26 or other personnel could be provided to the manufacturer and/or the integrated orthopedic system manager 74 (in the form of digitized data). In this alternative exemplary implementation, the process 10 can continue from block 100 to block 180. In yet another alternative, a mold or physical model of the bone or bone joint could be provided by the surgeon 26 or other personnel and digitized by the manufacturer or another third party that receives the mold or physical model. The digitized data of the mold and/or physical model could then be inputted into the orthopedic system manager 74. For discussion purposes only, the process 10 will continue with reference to the exemplary implementation shown in FIGS. 1-5.

During the consultation, any desired activities and/or lifestyle goals 36 of the patient 34 can be determined at block 150. According to one example, the patient 34 can identify physical activities that they desire to participate in, including those outside of or in addition to daily living. In this regard, some patients may desire a knee joint prosthesis that can provide the patient with a range of motion suitable for participating in physical activities such as, by way of example, yoga, downhill skiing, kick-boxing, rowing, etc. These lifestyle goals/activities 36 can be transmitted electronically via the network 22 to the server 46 of manufacturer 38 at block 152. For example, the surgeon 26 can access the integrated orthopedic system manager 74 via the user interface or web portal 70 or directly via access criteria and/or installed programs on the surgeon's user device 18.

In block 156, a 3-D model 160 (FIG. 12A-12B) of the bones in the X-ray data 116 can be created. In one exemplary implementation, initiation of the generation of the 3-D Model 160 can occur manually via user input to a local user device 18 associated with the network 22 and server 46 in connection with the integrated orthopedic system manager 74. In one exemplary implementation, the integrated orthopedic system manager 74 can initiate generation of the 3-D model 160 automatically upon receipt of the X-ray data 116. In this exemplary implementation, the automatic generation can commence without user input. With particular reference to FIG. 2, the integrated orthopedic system manager 74 can access a database of 3-D bone model data 164 (e.g., knee joint in this instance) at block 166. At block 168, the integrated orthopedic system manager 74 can access commercially available statistical shape modeling software 170 at datastore 56. The integrated orthopedic system manager 74 can use the statistical shape modeling software 170 to reconstruct the 2-D X-ray data 116 into the 3-D bone model(s) 160 at block 172, as generally shown for example in FIG. 12A. The commercially available statistical shape modeling software is available from various vendors or developers, such as, for example, Materialise USA, Ann Arbor, Mich. In one exemplary implementation, the database can include generalized knee joint 3-D bone model data 164 gathered over time from previous surgeries. It should be appreciated that CT or MRI image data could optionally be segmented, including manually, to generate the 3-D model.

Another alternative could include using uploaded photographic image data together with anthropomorphic data to generate the 3-D model.

The 3-D bone model data 164 can include defined anatomical landmark data for preoperative planning. The statistical shape modeling software 170 can generate a best fit 3-D statistical representation (i.e., 3-D model 160) of the 2-D X-ray data 116 with identified anatomical landmarks 174 (FIG. 12B) for surgical planning and execution. Use of the database of 3-D bone model data with pre-defined landmarks in connection with the statistical shape modeling software can significantly reduce the time and resources required to generate the 3-D bone model 160 for preoperative planning.

Once the 3-D model 160 is generated, the integrated orthopedic system manager 74 can generate a preliminary preoperative surgical plan 176 at block 180. In one exemplary implementation, the preoperative surgical plan 176 can be automatically generated without user input. The preliminary preoperative plan 176 can be prepared for surgeon or other medical user 26 review, and can include the planning of various bone resections, sizes and types of implants, and various geometric requirements including relevant dimensions, such as height, width, orientation of particular features, etc. The preliminary preoperative surgical plan 176 can include a recommendation of particular implants and associated instrumentation and/or guides to be used in the surgical procedure, as discussed below.

In one exemplary implementation, the preoperative surgical plan 176 can take into account the patient's medical history as provided by the surgeon 26 and/or available in the patient's master data file. Such patient history can include data related to previous orthopedic surgeries and/or consultations that may not have resulted in a surgery, both of which can be utilized by the integrated orthopedic system manager 74 in connection with a determination or identification of disease progression in generating the preoperative surgical plan 176. The patient history can also be utilized by the integrated orthopedic system manager 74 in connection with the determination or identification of disease progression in postoperative outcome reports, as will be discussed in greater detail below.

The preoperative surgical plan 176 can be generated automatically in the manner discussed above. In this regard, through leveraging the database of 3-D bone model data 164 with defined landmarks for surgical planning in connection with use of the statistical shape modeling software, the integrated orthopedic system manager 74 can generate the preliminary preoperative surgical plan 176 (and any optional plans 176' discussed below) in a short timeframe, such as less than 30 minutes. In one exemplary implementation, the plans 176 and 176' can be generated and provided to the surgeon 26 for review in under fifteen minutes from receipt of the X-ray data, and in some instances, in about five to ten minutes.

Such rapid turnaround times can significantly increase a surgeon's efficiency and practice options. For example, with the benefits of process 10, the surgeon could review the preoperative surgical plan 176 with the patient 34 during the same visit or day as the initial consultation (provided the imaging center is near or within the surgeon's office/practice). In another example, the rapid turn around times of process 10 can provide for preoperative planning for certain trauma cases.

While the preliminary preoperative surgical plan 176 has been discussed as being automatically generated, it will be appreciated that the generation of the preoperative surgical plan can be automatic, semi-automatic or manual. In one exemplary implementation, the generation of the preliminary preoperative surgical plan 176 can be automatic or substantially automatic as discussed above, but can be initiated manually.

The preliminary preoperative surgical plan 176 can be in the form of digital images that can be viewed interactively using a computer modeling software, such as the software 74 referenced above. The preliminary preoperative plan 176 and any further changes or a finalized preoperative plan 176 can be a plan devised to obtain a healthy or as close to healthy anatomical orientation after an operative procedure. The healthy anatomy can be based on natural or pre-injury anatomy or mechanically correct or efficient anatomical orientation.

With additional reference to FIG. 3, generating the preoperative surgical plan 176 can include incorporation of surgeon preferences 182 at block 184. The surgeon preferences 182 can be stored in and accessed from, for example, a surgeon information file or database 188 at datastore 56, as generally shown in FIG. 8. At block 192, an optional desired range of motion can be determined based on the previously transmitted and stored activity/lifestyle goals 36 of the patient 34. Those skilled in the art will readily appreciate that certain physical activities can require a range of motion that may be different than other physical activities. Such range of motion information, in certain instances, can be a factor in selecting or recommending an implant for a patient. An implant type can be determined at block 196 and an implant size can be determined at block 200. As will be discussed in greater detail below, the implant type and size 196, 200 can be associated with a standard implant or can drive creation of a custom implant, such as a patient specific implant, from the patient data and information in datastore 56. Initial implant placement can be determined at block 204.

The preoperative surgical plan 176 can include or be saved as a data file, in the datastore 56 associated with the manufacturer 38 and the server 46. The data file can be any appropriate type including image data, patient data, resection area data, recommended implants and instrumentation, etc. As discussed above, the preoperative surgical plan 176 can be generated by the manufacturer 38 via the integrated orthopedic system manager 74. As also discussed above, the manufacturer can be any appropriate manufacturer or service provider 38, such as an implant and/or guide manufacturer or specification producer. A specification producer can be a service that provides specifications for an implant or guide to a manufacturer for production.

In one exemplary implementation, the automatic generation of the preoperative surgical plan 176 can stop or "fail out" during any aspect of the plan generation (e.g., segmentation, implant recommendation, instrumentation recommendation, etc.) if any one of a number of predetermined criteria are not met. In one example, the software 74 can include a reliability scale or reliability criteria and a predetermined reliability threshold can be inputted as determined, for example, by the manufacturer 38. If the fail-out criteria fall below the predetermined threshold or the preoperative surgical plan 176 does not meet the reliability criteria, the preliminary preoperative plan 176 can be flagged, by the software 74, for review by the manufacturer 38. At this point, the process 10 can stop or be placed on hold until such review and manual intervention or input (e.g., revisions and/or authorization to proceed) is received to continue process 10.

In one exemplary implementation, specific reasons for any preliminary preoperative plan 176 that required manual review due to a fail-out during the planning process can be fed back or incorporated as fail-out criteria or weighted fail-out criteria for future preoperative planning (to the extent not already being utilized). In this exemplary implementation, and with reference to a successful surgery that experienced a fail-out during the planning process and was successfully resolved, the resolution can be incorporated into the software 74/process 10 to enhance the robustness of process 10.

In one exemplary implementation, various aspects of the generated preoperative surgical plan 176 can be cross-validated, such as by providing the plan 176, or various aspects thereof, through multiple software packages or algorithms. This cross-validation can be in addition to or in lieu of the fail-out processes discussed above.

The preoperative surgical plan 176 can be provided to or accessed by the surgeon via notification or surgeon access at block 208 of FIG. 1. The access, notification or delivery of the preoperative surgical plan 176 can be via an Internet or worldwide web connection, cellular connection, etc. to or via the user device 18 associated with the surgeon. In one exemplary implementation, the integrated orthopedic system manager 74 can notify the surgeon 26 or delegated user that the preliminary preoperative plan 176 is ready for review. The notification that the preoperative plan 176 is prepared and ready for review can be performed in any appropriate manner. For example, an e-mail notification can be sent to the surgeon 26 or a text message can be sent to the surgeon 26.

In one exemplary aspect, a physical model of the bone or bone joint associated with the preoperative surgical plan 176 could also be generated and provided with or as part of the preoperative surgical plan 176 to the surgeon 26. In one exemplary implementation, the integrated orthopedic system manager 74 can include an option for the surgeon 26 or another administrator to select up-front whether a physical model is desired to accompany the preoperative surgical plan 176. It will be appreciated that the preoperative surgical plan 176 could utilize the physical model in addition to or in lieu of the 3-D model 160. It will also be appreciated that the preoperative surgical plan could utilize a 2-D model in lieu of or in addition to the 3-D model 160.

Once the surgeon 26 is notified that the preoperative plan 176 is ready for review, the surgeon 26 can access the preoperative plan 176 at block 212 for review. In one exemplary implementation, the surgeon can log into the integrated orthopedic system manager 74 program via user interface or web portal 70 in the manner discussed above. The surgeon 26 can access the preoperative plan 176 in one of a plurality of ways at block 212. For example, the surgeon 26 can download the preoperative plan 176 to a handheld user device or computer terminal 18 on which appropriate software is installed to access the preoperative plan 176. The surgeon 26 may also view a printout of the preoperative plan 176 for manipulating or commenting on the preoperative plan 176.

Alternatively, or in addition thereto, the surgeon 26 can access the server 46 to review the preoperative plan 176 in the datastore 56 of server 46 of the manufacturer 38. The integrated orthopedic system manager 74 can, upon access by the surgeon 26, cause the surgeon's user device 18 to display an interactive display or user interface, such as the exemplary user interface 218 shown in FIG. 13A, for the surgeon 26 to review, approve and optionally edit the preoperative surgical plan 176.

If the user device 18 accesses the preoperative plan 176 on the processor, datastore 52, 56, the user device 18 need only display the interactive user interface 218 representing a portion of the file on a display screen 226 of user device 18. That is, the preoperative plan 176 and any edits or processing made to the preoperative plan 176 can be done solely or substantially by the processor 52 that executes a program to manipulate and display the file. The processor 52 and the datastore 56 need not be physically near or connected to the user device 18. The user device 18 can be provided to display the interactive user interface 218 and may not be required to process the preoperative plan 176 file from the manufacturer, but only be provided to display the preoperative plan 176 file and receive and transmit input from the surgeon 26. Any inputs or edits can be directly transmitted to the server 46 for processing augmentation or editing of the file.

With particular reference to FIGS. 1, 4 and 13A-14B, the surgeon 26 can review the preoperative surgical plan 176 for approval at blocks 212 and 228 of FIG. 1. As part of the review, images 232 (FIG. 13A) of the 3-D bone model 160 can be reviewed with the patient 34 at block 236 of FIG. 4. The 3-D models 160 can be provided for the surgeon 26 as part of the preoperative surgical plan file, or as a separate file, both of which can be accessible from the user interface 218. The surgeon 26 can review images 232 of the 3-D model 160 with the patient 34 via portable user device 18. In the exemplary implementation illustrated in FIG. 13A, the surgeon 26 can review an image 232A of the 3-D bone model 160 of the patient's bone as reconstructed from the X-ray data 116. The surgeon 26 can then, for example, review an additional image 232B showing the recommended or approved implants for the surgical procedure, as shown in FIG. 13B.

Figure 13B:
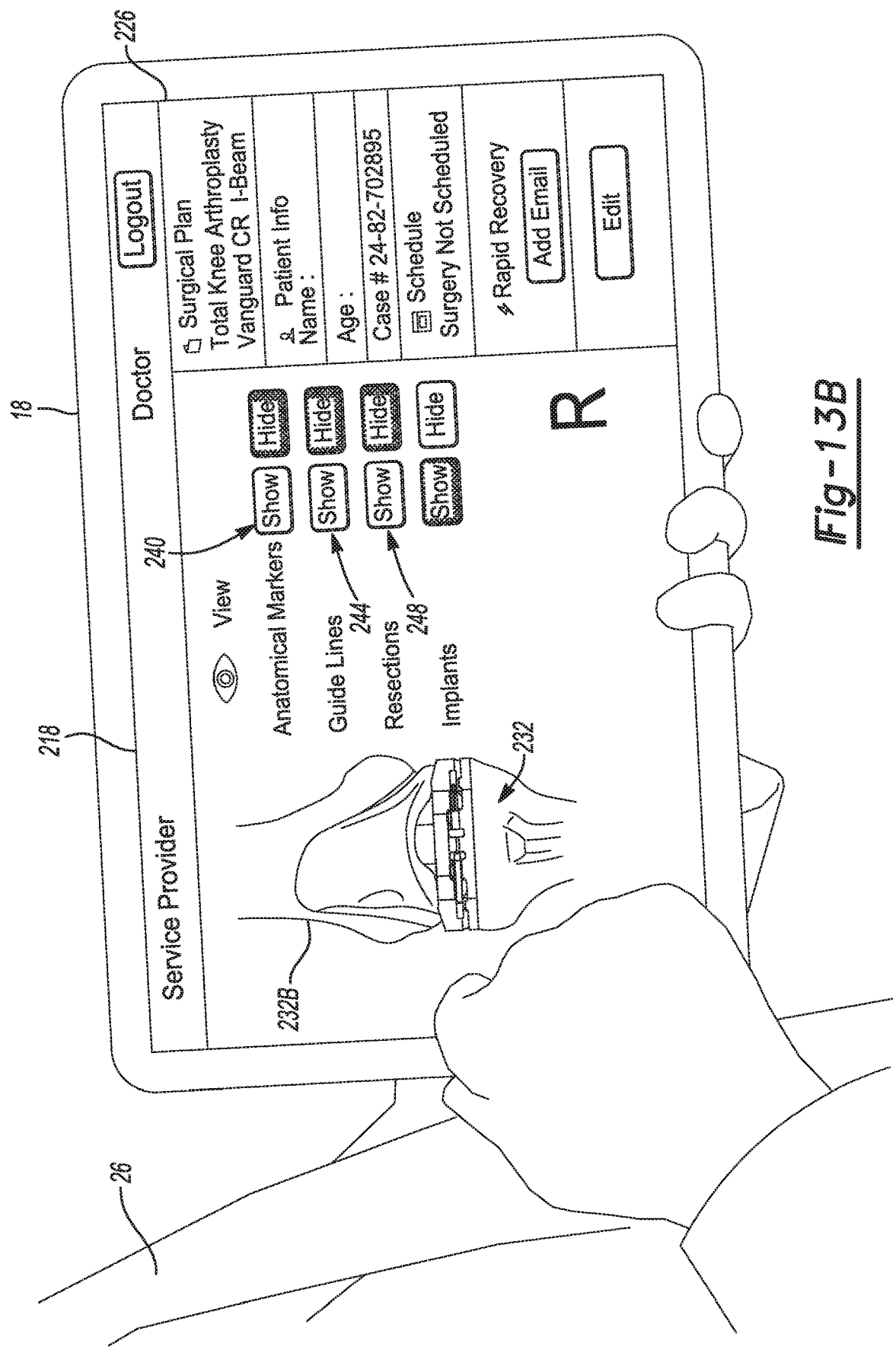
FIG. 13B is a view of an exemplary display or user interface illustrating an aspect of a preoperative surgical plan for review with a patient according to an aspect of the present disclosure.

As can be seen in FIGS. 13A and 13B, various other aspects of the surgery and/or preoperative plan 176 can be reviewed with the patient 34. For example only, the surgeon or user 26 can optionally review images showing anatomical markers by selecting option 240, guide lines by selecting option 244 and resections by selecting 248. The surgeon 26 can select those and other options by touching the appropriate area of the displayed user interface 218 with a finger, stylus, etc., for example.

Figure 14A:
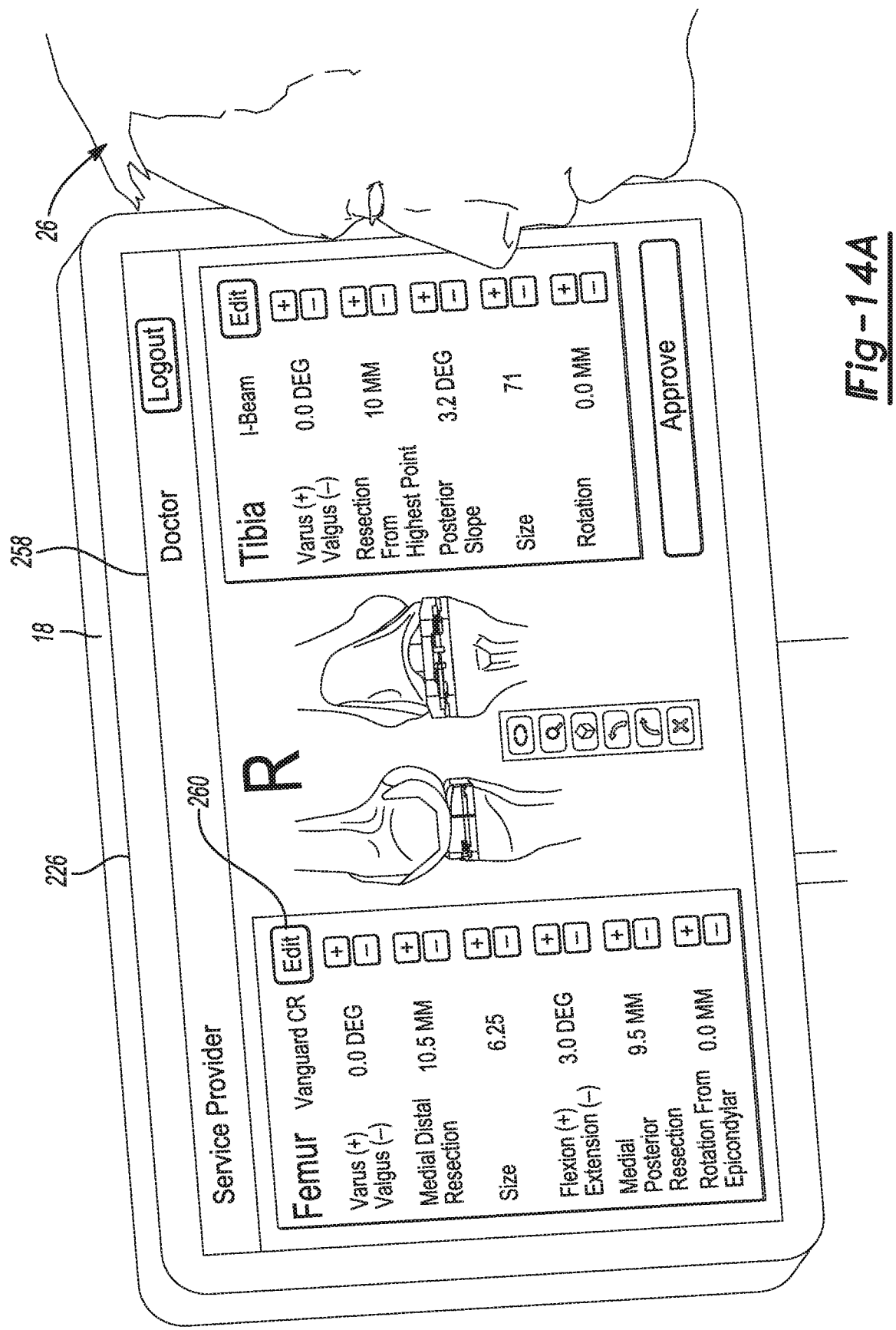
FIG. 14A is a view of an exemplary display or user interface illustrating an aspect of a preoperative surgical plan for review by a surgeon according to an aspect of the present disclosure.
Figure 14B:
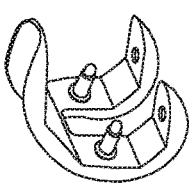
FIG. 14B is a view of an exemplary display or user interface illustrating an aspect of a preoperative surgical plan for review by a surgeon according to an aspect of the present disclosure.
Figure 15:
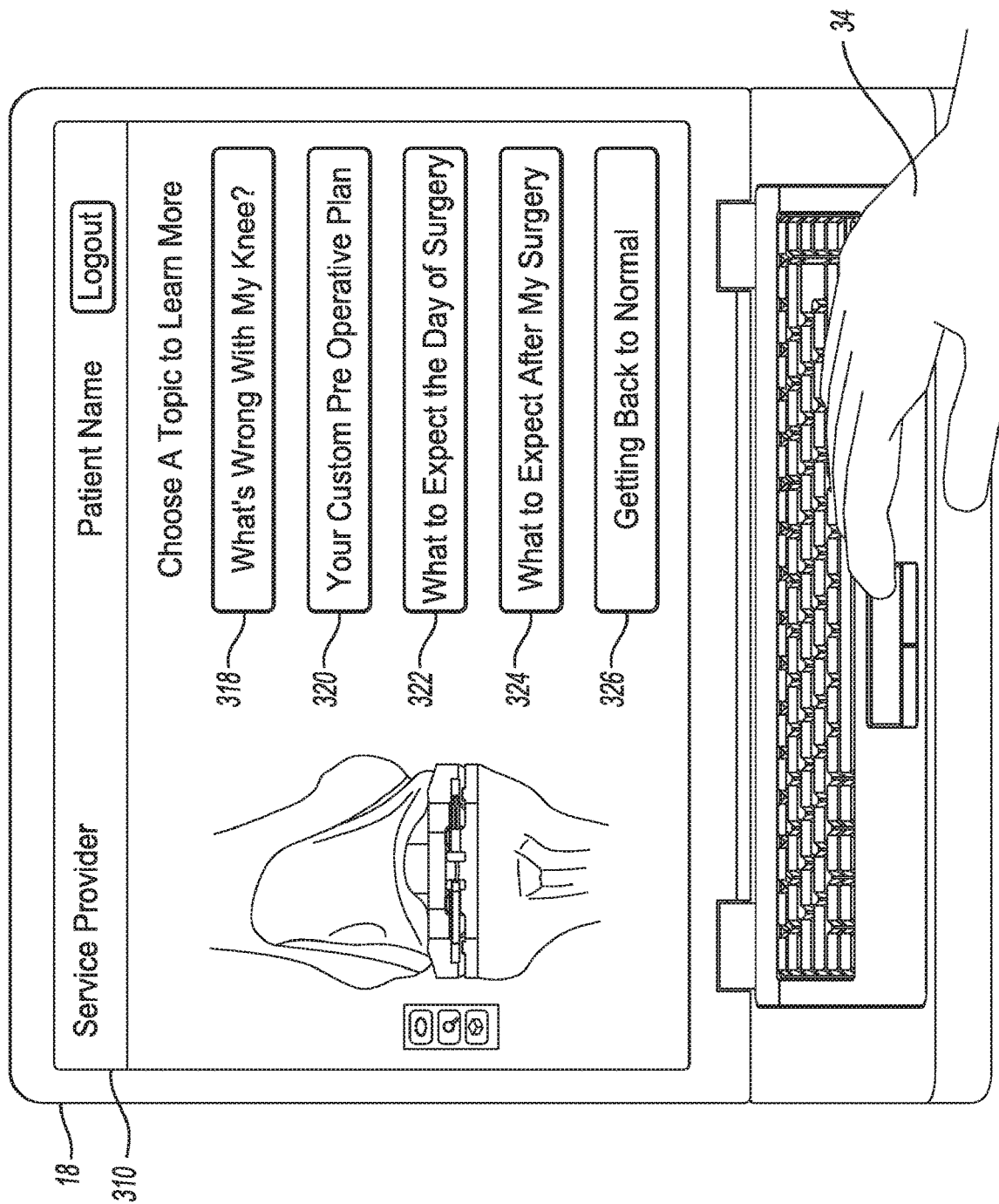
FIG. 15 is a view of an exemplary display or user interface illustrating patient information according to an aspect of the present disclosure.

At block 254 of FIG. 4, the surgeon 26 can review the recommended implant in the preoperative plan 176 and make an implant selection (e.g., approval of the recommended implant) in an interactive user interface 258 displayed at user device 18, as shown for example in FIG. 14A. The surgeon 26 can optionally select a different implant by selecting the edit option 260, which can cause the integrated orthopedic system manager 74 to display at the user device 18 additional/other implant options for review by the surgeon 26. The integrated orthopedic system manager 74 can be configured to only display implant selections/procedures that are approved for use and/or can optionally not show implant selections the particular surgeon 26 has previously indicated (such as in the surgeon preferences) are not preferred options. In one exemplary implementation, the integrated orthopedic system manager 74 can access a database 266 (FIG. 8) at datastore 56 in connection with displaying the additional implant options.

Specifically, the surgeon's selection of an implant can include any one of the following three options: a first option of a custom or patient-specific implant or a second option of a semi-custom made implant, or a third option of a standard or off-the-shelf implant. It will be appreciated that, based on the surgeon's selection/revision, the preliminary preoperative surgical plan 176 may need to be modified and then resubmitted to the surgeon 26 for approval. A more detailed discussion of such implant options can be found in commonly owned, co-pending patent application Ser. No. 12/973,214, filed on Dec. 20, 2010, which is incorporated by reference herein. At block 262 of FIG. 4, the surgeon 26 can make other plan adjustments or edits, including positional adjustments, cut or resection line adjustments, implant size adjustments, etc. Any such adjustments or edits can be automatically transmitted to server 46 and incorporated into the patient's master data file 154.

The surgeon 26 can also review recommended instrumentation in a user interface 268 for the surgical procedure provided as part of the preoperative plan 176 at block 272. It should be appreciated that user interface 268 can be the same or a different user interface as user interface 258. The recommended instrumentation can be determined in part by the integrated orthopedic system manager 74 in connection with the surgeon preferences 182 saved in datastore 56. The recommended instrumentation can be updated based on the surgeon 26 choosing a different implant option than was initially recommended with the preoperative surgical plan 176. In this regard, the integrated orthopedic system manager 74 can be configured to flag, such as with a note to the surgeon 26, that the surgeon's optional implant selection may require instrumentation that he has previously indicated was not preferred (e.g., in surgeon preferences 184) and/or is incompatible with the optional implant selection. The integrated orthopedic system manager 74 can, for example, include data on instrumentation compatibility in database 266.

In the exemplary implementation illustrated, the user interface 268 can include an instrument selection area 274 and a guide selection area 278 if applicable. In this regard, the surgeon 26 can select to use reusable instruments, or disposable instruments or a combination thereof. Either set of instruments can be preset with settings corresponding to the preoperative plan 176, including the implant selected and the surgeon's preferences 182. In one exemplary implementation, should the surgeon 26 select to use standard instrumentation not to be provided by the manufacturer 38, the integrated orthopedic system manager 74 can provide instrument settings for the instruments to be used by the surgeon 26 based on the stored surgeon's preferences 182 and the implant selection.

The surgeon's review of the surgical plan 176 may further include a request for one or more patient-specific alignment guides to be used with the selected implant. The surgeon can make such a selection via the guide selection area 278 of user interface 268. Exemplary patient-specific alignment guides are described in co-pending patent application Ser. No. 11/756,057, filed on May 31, 2007, Ser. No. 11/971,390, filed on Jan. 9, 2008, Ser. No. 12/025,414, filed on Feb. 4, 2008, and Ser. No. 12/039,849 filed on Feb. 29, 2008. The alignment guides can be manufactured by rapid prototyping methods, such as stereolithography or other similar methods or by CNC milling, or other automated or computer-controlled machining or robotic methods, and cleaned.

The user interface 268 can also provide the option for selection by the surgeon of specific implant kit contents. An implant kit can include standard contents for implantation of an off-the shelf implant or various different configurations of custom or semi-custom implants with surgeon approved instrumentation, guides and/or trials. By providing the surgeon 26 with the option to specify desired contents of the surgical kit for the procedure associated with the preoperative surgical plan 176, inventory requirements both at the manufacturer 38 and the hospital can be reduced and more efficiently managed.

With reference back to FIG. 1, the surgeon 26 can, after review of the preoperative plan 176 (including any edits thereto), approve the preoperative plan 176 at block 282. Any changes or edits to the preoperative plan 176 made by the surgeon 26 can then be saved to the preoperative plan 176 file to generate an edited preoperative plan file. If the surgeon 26, after review of the preoperative plan 176 in block 212, finds the plan to be unacceptable, the "No" path 286 can be followed, where the surgeon's rejection of the plan can be transmitted by manufacturer 38 via the integrated orthopedic system manager 74.

With reference back to blocks 178 and 208 of FIG. 1, integrated orthopedic system manager 74 can, in addition to the preoperative plan 176 provided to the surgeon 26 at block 208, generate optional alternative preoperative surgical plans 176' and provide the same to the surgeon for review and approval at block 208'. For example, the integrated orthopedic system manager 74 can generate the preliminary preoperative surgical plan 176 for the total knee replacement in the manner discussed above. In addition thereto, the integrated orthopedic system manager 74 could also generate other optional preoperative surgical plans 176' such as a partial knee replacement (femur or tibia) or a unicondular knee replacement, for example. This process can provide for improved efficiency and a reduction in any rejections of the preoperative plans by providing various options to the surgeon for review and approval at the same time. Moreover, by leveraging the database of 3-D bone model data 164 with defined anatomical landmarks and the statistical shape modeling technology, the integrated orthopedic system manager 74 can also generate these reports automatically without user input and without any significant or notable additional time requirement.

Upon approval of the preliminary preoperative surgical plan 176 or optional surgical plan 176' (hereinafter preoperative plan 176), the patient can be sent to the scheduler 42 at block 290 of FIG. 1 for scheduling the surgical procedure. The scheduler 42 can access the integrated orthopedic system manager 74 via web portal or user interface 70 in the manner discussed above. Alternatively, the scheduler could have direct access to the integrated orthopedic system manager 74 for scheduling purposes. Regardless of the access method, the scheduler 42 can schedule a surgery date for the patient 34 at block 290 using the integrated orthopedic system manager 74.

With the preoperative plan 176 approved and the surgery date scheduled, the integrated orthopedic system manager 74 can provide relevant information to a manufacturing planning system 298 (FIG. 6) of the manufacturer 38 at block 302 of FIG. 1. This aspect of process 10 can serve to increase manufacturing efficiency and planning by having information regarding implants, instrumentation, guides and/or trials likely to be sold early in the surgical planning process. Further, inventory can be more efficiently managed and/or reduced based on the information available from the surgeon approved preoperative plan 176 and surgical kit content selection. In one exemplary implementation, the integrated orthopedic system manager 74 can access a manufacturing database 304 at datastore 56 (FIG. 8) that can be part of or separate from the manufacturing planning system 298 of manufacturer 38.

Figure 1A:
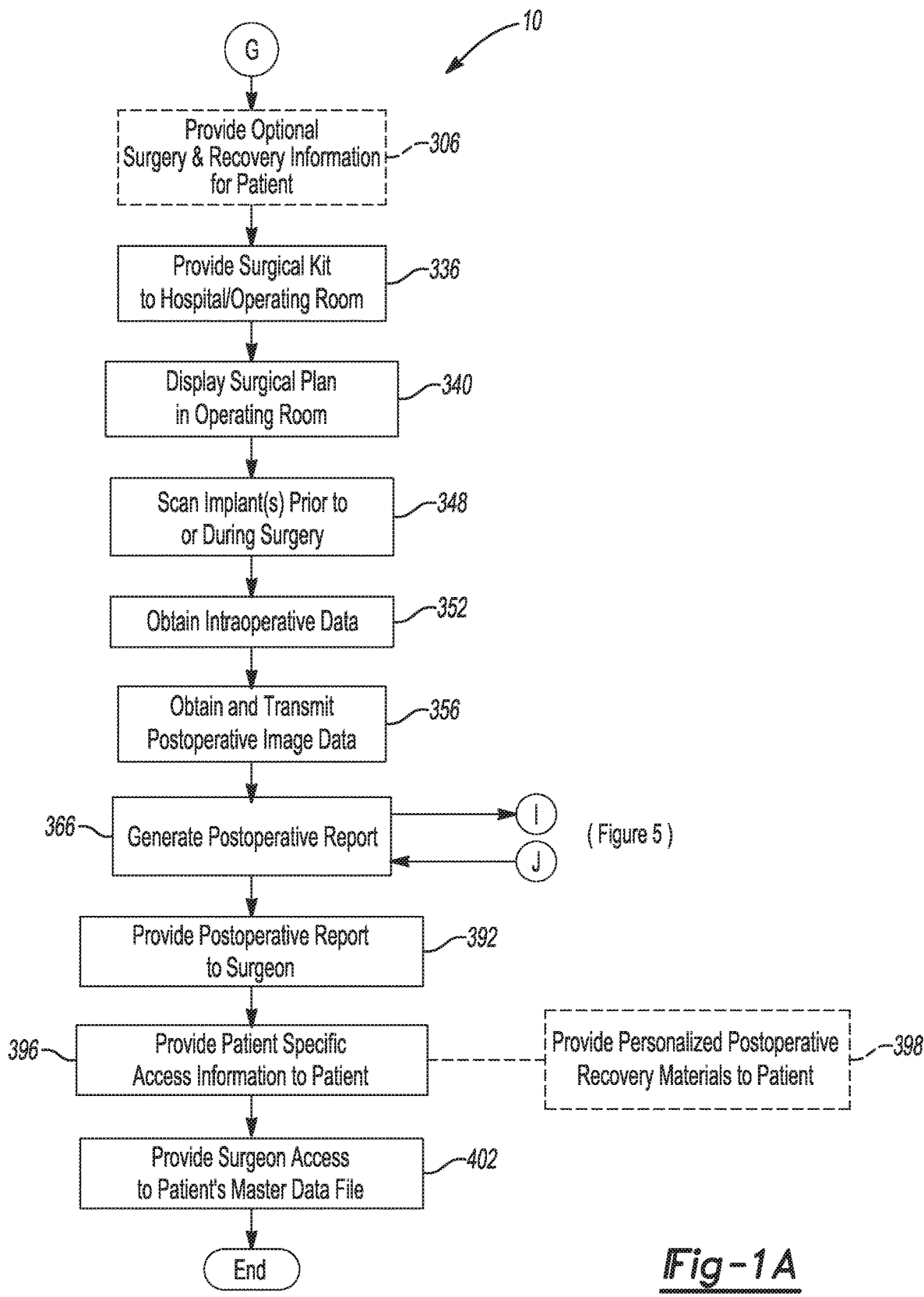
FIG. 1A is a continuation of the flowchart of the digitally integrated orthopedic process of FIG. 1 according to an aspect of the present disclosure.

With particular reference to FIG. 1A, process 10 can continue with optional surgical planning and recovery information being provided to the patient 34 at block 306. In one exemplary implementation, the information can be automatically provided to a user device 18 of the patient 34, such as the laptop computer shown in FIG. 15. The patient 34 can access the information in any suitable manner, such as via web portal or user interface 70, through a link provided in an e-mail sent to the patient, etc. Regardless of the access method, the patient 34 can access the integrated orthopedic system manager 74, which can cause, in the exemplary implementation illustrated in FIG. 15, an interactive user interface 310 to be displayed on the patient's user device 18.

The information provided to patient 34 can be tailored to the patient based on the preoperative plan 176, and, in one exemplary implementation, can include information and materials related to recovery in connection with the patient's lifestyle goals/activities 36. The information can be accessed from datastore 56 in one or both of the patient master data file 154 and/or a recovery and educational materials database 314. The surgeon 26 can, through interaction with integrated orthopedic system manager 74, specify the information to be made available to patient 34.

In the exemplary configuration illustrated, the user interface 310 can provide access to information relating to the injury to the patient's knee joint at selection option 318, information relating to the patient's customized preoperative plan 176 (which can be all or a portion of the plan made available to surgeon 26) at selection option 320, information relating to the day of surgery at selection option 322, information relating to the postoperative care at selection option 324 and information relating to recovery at selection option 326. As can also be seen in FIG. 15, various images can be displayed in user interface 310 corresponding to various selections made by the patient 34.

It should be appreciated, however, that access to more or less than the information discussed immediately above can be provided to patient 34 via user interface 310. In one exemplary configuration, the surgeon 26 can be provided with an option during the preoperative plan approval process to select from a database in the datastore 56, such as the recovery and education materials database 314 (FIG. 8), various types of information materials to be made available to the patient 34. The surgeon 26 could also be provided with an option to select specific times (e.g., before and after surgery) at which to provide or make available certain specific information to the patient 34. In one exemplary implementation, the integrated orthopedic system manager 74 can recommend information to be made available to the patient and the surgeon 26 can approve or modify the recommended information, including an option to not send information to the patient. In one exemplary implementation, the integrated orthopedic system manager 74 can include a process by which surgeon 26 approval is required before any information is sent to the patient. In one exemplary implementation, preferences of the surgeon 26 with regard to information to be provided to patient 34 can be stored in the datastore 56.

Referring back to FIG. 1A, the process 10 can continue at block 336 with the surgical kit selected by surgeon 26 being delivered to the hospital or operating room. In one exemplary implementation, the surgical kit can be the patient-specific customized kit selected by the surgeon 26 during approval of the preoperative plan 176. Delivering the customized surgical kit can reduce the labor involved in preparing a traditional joint replacement case. For example, in one exemplary implementation, only the guides, trials, instrumentation and implants required for the surgery are delivered. The process 10 and the preplanning associated therewith can also provide for just-in-time delivery of the customized surgical kit thereby reducing inventory requirements and complexity for both the manufacturer 38 and the hospital or medical facility. The process 10 contemplates the surgical kit or kits being assembled by the manufacturer 38, the hospital or other medical facility, and/or a third party directed by the manufacturer 38, such as an assembler or distributor. The kit could also be assembled, at the direction of the manufacturer 38, by one or more of the parties listed immediately above.

In one exemplary implementation, the process 10 can include providing a data file for instrumentation to be included with the surgical kit, and the hospital or another third party can manufacture the specified instrumentation for inclusion in the kit. In one example, the hospital can receive the instrumentation data file and manufacture the instruments and assemble the kit. The instruments can be manufactured using various rapid manufacturing techniques, such as stereo lithography and 3-D printing.

Figure 16A:
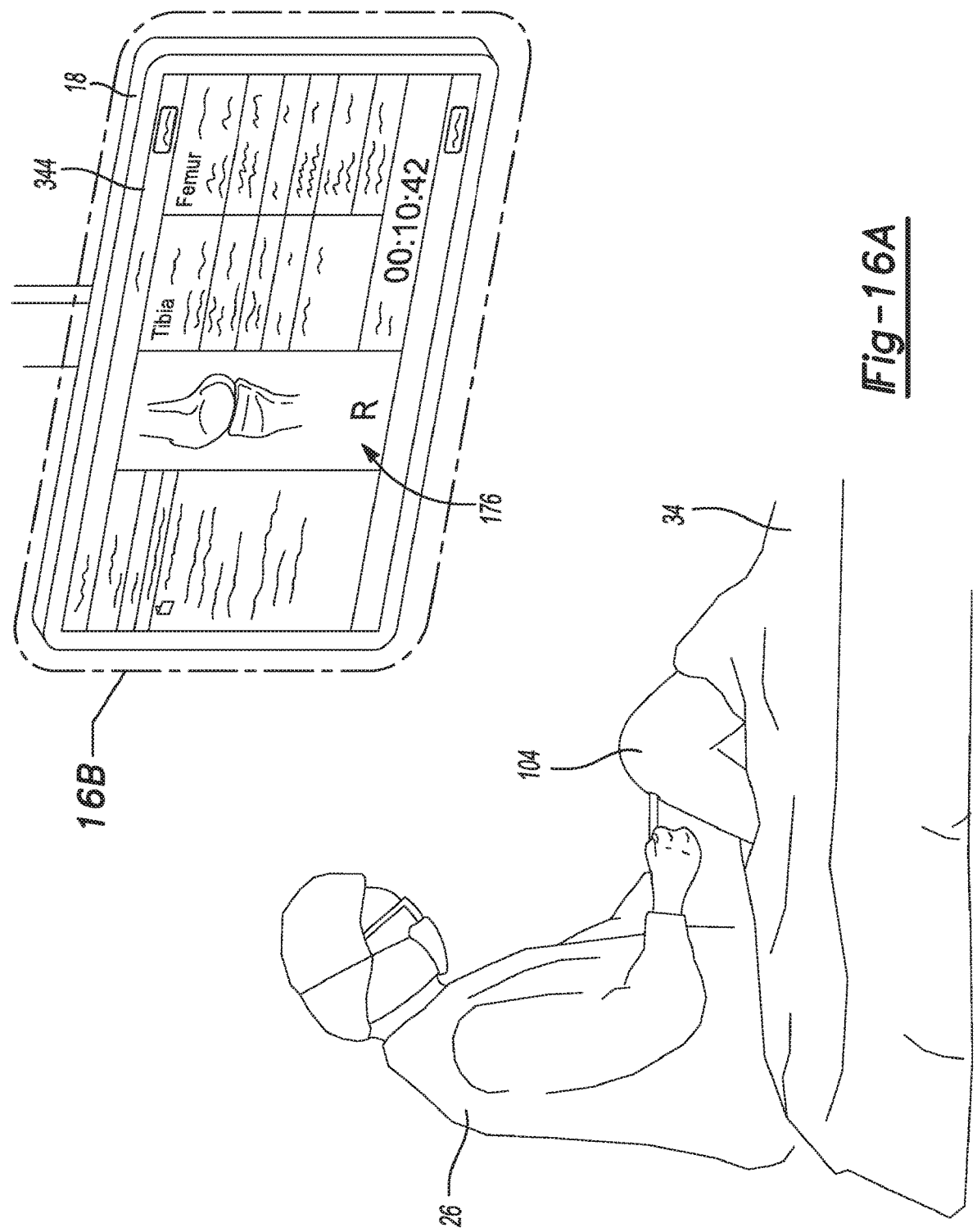
FIG. 16A is a perspective view of an exemplary surgical procedure in an operating room with a preoperative surgical plan displayed on a user or client device according to an aspect of the present disclosure.

The process 10 can continue at block 340 where the approved surgical plan 176 can be accessed and viewed in the operating room using various display options, including a client device 18. Other display options can include a heads-up display, visors, and/or a hard copy of the approved surgical plan 176, such as a printed copy. The optional physical model can also be utilized in the operating room. In the exemplary configuration illustrated, the surgical plan 176 can be accessed via the web portal or user interface 70 though an Internet connection 22 in the manner discussed above. The integrated orthopedic system manager 74 can cause the operating room client device 18 to display an interactive user interface 344 including details of the surgical plan 176 in real time, as shown in FIG. 16B with reference to FIG. 16A.

The surgical team in the operating room can interact with the interactive user interface 344 to display various aspects of the surgical plan 176 via the various selection options presented in user interface 344, as shown in FIG. 16B. In one exemplary implementation, the user interface 344 can be customizable to specific preferences for each surgeon user 26. Such preferences can be maintained in the datastore 56, for example in the surgeon information database 188. Any notes or special instructions provided by the surgeon 26 to the integrated orthopedic system manager 74 during approval of the preoperative plan 176 can be displayed in user interface 344 for viewing during the surgical procedure.

Prior to or during surgery, the implants delivered for the patient 34 can be verified by the surgeon 26. In one exemplary implementation, a handheld or other user device 18 can scan an identification code or information tag associated with the delivered implants and transmit this code/tag or information associated therewith to the integrated orthopedic system manager 74 via the user interface 344 or another access method to integrated orthopedic system manager 74. In one exemplary implementation, the information tag or code can be a barcode. The information can be transmitted wirelessly or entered via the user interface 344. At block 348, the integrated orthopedic system manager 74 can compare the transmitted implant identification information with the implant identification information in the surgical plan 176 and provide visual confirmation via user interface 344 that the delivered implants match the implants identified in the surgical plan 176. Instrumentation to be used with the surgery can also be scanned prior to or during surgery and compared with instrumentation identification information in the surgical plan 176.

In one exemplary implementation, scanning the kit, implants and/or instrumentation at block 348 can automatically cause the integrated orthopedic system manager 74 to load and/or display the surgical plan on the user device 18 associated with the operating room and/or the device used to perform the scanning.

During surgery, various intraoperative data can be obtained at 352 and transmitted or uploaded to the server 46 via the user interface 344 or another user interface in the operating room providing access to the integrated orthopedic system manager 74. Data and/or notes from the surgeon 26 and/or surgical team can be transmitted or uploaded to the server 46. In one exemplary implementation, any notes, data, etc. that are generated or captured during the surgical procedure can be associated with corresponding times of surgery and stored in the patient's master date file 154. The integrated orthopedic system manager 74 can also include various software systems and/or sensors to record, capture, analyze, etc. data associated with the surgical plan 176, including intraoperative data. In one exemplary implementation, one or more of the various software programs can be integrated with the orthopedic system manager 74 and provided from the server side. In one exemplary implementation, one or more of the various software programs can be associated with the user device on the client side and utilized in connection with the orthopedic system manager 74.

In one example, body temperature data can be captured and monitored during surgery relative to one or more predetermined thresholds. In another example, knee kinematic data can be obtained intraoperatively and transmitted and saved in the patient's master data file 154. In one exemplary implementation, the knee kinematic data can be obtained using OrthoSensor's commercially available Verasense™ instrumented trail bearing. The kinematic data can include or be combined with force data. In this example, the data can be captured intraoperatively and analyzed, locally or remotely, and real-time feedback can be provided via the integrated orthopedic system manager 74 and user interface 344. Feedback can include, among other things, a validation of implant positioning and/or an analysis of kinematic data as compared to predetermined data or thresholds. This feedback can occur intraoperatively in the operating room. Any notes or observations from the surgeon 26 or team members can be transmitted to the patient's master data file 154 via the user interface 344.

With continuing reference to FIG. 1A, postoperative image data, such as X-rays 360, showing the implants can be taken and transmitted to the integrated orthopedic system manager 74 at block 356 in one of the various manners discussed above for X-ray data 116, such as via the user interface or web portal 70. A postoperative report 362 can be generated at block 366 by the integrated orthopedic system manager 74 and stored in the patient's master data file 154 in datastore 56. The post-operative image data 360 can be obtained at various times post surgery, including immediately or substantially immediately thereafter, thirty days, six weeks, six months, one year, etc.

With additional reference to FIG. 5, generating the postoperative report 362 can include generating a postoperative 3-D model 370 of the patient's bones with the implants implanted at block 374. The postoperative 3-D model 370 can be generated using the statistical shape modeling software 170, models of the implants scanned from the operating room, and the transmitted postoperative X-ray data 360 and stored in the patient's master data file 154. Similar to the preoperative 3-D bone models 160, the postoperative 3-D models 370 can be generated in a short timeframe, e.g., less than ten minutes, and thereafter provided to the surgeon 26 for review and analysis in a similar manner as the preoperative surgical plan 176.

It will be appreciated that other forms of data can be obtained post surgery and utilized in connection with the postoperative report 362. For example, the postoperative report 362 can include or utilize other forms of data in addition to and/or in lieu of the above discussed image data, including audible data, ultra sound data, vibration data and analysis, etc. The postoperative report 362 can also include data from the patient pertaining to the patient experience with the implant or implants. This patient experience data can be obtained at one or more of the various different times post surgery discussed above, as may be determined by the surgeon 26. The patient experience data can be uploaded or transmitted to the patient's master data file 154 via the integrated orthopedic system manager 74 and the surgeon's user device 118 in one of the manners discussed above. In one exemplary implementation, the integrated orthopedic system manager 74 can generate a new or updated postoperative report 362 and provide the same to the surgeon 26 each time new or additional postoperative data is provided to the integrated orthopedic system manager 74.

The postoperative report 362 can be a report with standard entries or can be a customized report that takes into account any surgeon 26 requests for inclusion in the report. In one exemplary implementation, such requests can be solicited by the integrated orthopedic system manager 74 during various stages of the preoperative planning process and can be stored in the surgeon preferences database 184.

At block 378, the integrated orthopedic system manager 74 can compare the preoperative plan 176 and the actual results of the surgical procedure, as captured in the postoperative 3-D models 370 and/or other forms of postoperative data discussed above. The postoperative report 362 can also include various other data or information, including predicted range of motion, any surgeon specified measurements or notes, as well as any intraoperative data, as noted in block 384. In this regard, the postoperative report 362 can include a patient satisfaction survey with data or information obtained from the patient 26, as well as other personnel and/or facilities involved with the procedure. As discussed above, at block 388 the postoperative report can be saved in the patient's master date file 154.

Returning to FIG. 1A, access to the postoperative report 362 can be provided to the surgeon at block 392 in a similar manner as the preoperative plan 176 discussed above. The postoperative report 362 can be reviewed by the surgeon 26 via the web portal 70 and can be used for immediate input to postoperative outcome studies for the surgeon 26. It should appreciated that while the postoperative report 362 is discussed above as being provided to the surgeon 26, the postoperative report 362 can be provided or made available to various potential users including, but not limited to, medical professionals, companies, organizations, regulatory bodies and/or registries. In one exemplary implementation, the surgeon 26 can specify which users may be provided with or given access to the postoperative report 362. In this regard, it will be appreciated that custom postoperative reports can be generated for different users (e.g., surgeon, regulatory body, etc.) based on the preferences and/or requirements of such users.

Shortly after the surgery, the integrated orthopedic system manager 74 can provide patient specific rapid recovery materials 394 (FIG. 8) to the patient 34 at blocks 396 and 398. The rapid recovery materials 394 can be provided automatically via e-mail as attachments and/or via a link in the e-mail to the user interface or web portal 70, from which the patient 34 can access the rapid recover materials 394 and any other aspects of the patient master data file 154 designated by the surgeon 26. Access information (e.g., login criteria) can also be provided to the patient 34 in the form of an information card or wrist band as an additional or alternative means of providing the access information to patient 34. The rapid recovery materials 394 can alternatively be automatically generated and provided to the patient 34 in hard copy form. In one exemplary implementation, the integrated orthopedic system manager 74 can specify recovery materials 394 to be provided to the patient 34, and the surgeon 26 can modify and/or approve the materials for sending to patient 34.

Continuing to block 402, access to the patient's master data file 154 stored in datastore 56 can be made available to the surgeon 26 for a predetermined period of time after the surgery. In one exemplary implementation, the predetermined period of time can be sixty days. In another exemplary implementation, the predetermined period can be while the file is active and 60 or 90 days thereafter. The surgeon 26 can access the patient's master data file 154 via the user interface or web portal 70 in the manner discussed above. The contents of the patient's master data file 154 can be made available for transmitting or downloading by the surgeon 26 during this predetermined period of time. Once the predetermined period of time has expired, patient specific data can be deleted. Generalized data of the patient's bone models, etc. can be used to populate the bone model databases of 3-D bone model data with defined anatomical landmarks discussed above.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The term software, as used above, may include firmware, byte-code and/or microcode, and may refer to programs, routines, functions, classes, and/or objects. The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions. It should be noted that the described process steps and instructions could be embodied in software, firmware or hardware, and when embodied in software, could be downloaded to reside on and be operated from different platforms used by real time network operating systems.

What is claimed is:

1. A system for generating a preoperative plan for an orthopedic surgical procedure, the system comprising:
    one or more processors;
    memory including instructions, which when executed by the one or more processors, cause the one or more processors to:
    retrieve, from a database, generalized data of previous bone models generated for orthopedic surgical procedures and surgical outcome information for the orthopedic surgical procedure;
    retrieve, from the database, patient-specific information related to the orthopedic surgical procedure, including range of motion data;
    automatically generate the preoperative plan for the orthopedic surgical procedure using the generalized data, the surgical outcome information, and the patient-specific information related to the orthopedic surgical procedure, operations to generate the preoperative plan including:
    select, with the one or more processors automatically, an implant based on the range of motion data;
    generate a patient-specific 3D model based on the patient-specific information and the generalized data of previous bone models; and
    render a visual depiction of the implant with the patient-specific 3D model; and
    output the preoperative plan for display on a user interface;
    receive postoperative image data; and generate a postoperative outcome study report including a comparison of the preoperative plan with the postoperative image data, wherein the comparison includes comparison of the 3D model to the postoperative image data, and wherein the outcome information includes range of motion data.

2. The system of claim 1, wherein the outcome information includes range of motion data.

3. The system of claim 1, wherein the patient-specific information includes an image of the patient.

4. The system of claim 1, wherein the instructions further cause the one or more processors to output a data file including instrumentation to be included with a surgical kit based on the preoperative plan.

5. The system of claim 1, wherein the user interface is presented on a heads-up display.

6. The system of claim 1, wherein the patient-specific information includes data generated or captured during a previous orthopedic surgical procedure for the patient.

7. The system of claim 1, wherein the orthopedic surgical procedure is a knee arthroplasty, and wherein the instructions further cause the one or more processors to:
obtain knee kinematic data intraoperatively;
analyze the knee kinematic data; and
provide real-time feedback via the user interface based on the analyzed knee kinematic data.

8. The system of claim 7, wherein the feedback includes a validation of implant positioning or an analysis of kinematic data as compared to predetermined data or a threshold.

9. The system of claim 1, wherein the instructions further cause the one or more processors to scan a machine readable code on a surgical kit, an instrument, or an implant selected based on the preoperative plan, and wherein the preoperative plan is automatically output for display on the user interface in response to scanning the machine readable code.

10. The system of claim 1, further including instructions, which when executed by the one or more processors, cause the one or more processors to:
receive postoperative image data;
generate a postoperative outcome study report including a comparison of the preoperative plan with the postoperative image data, wherein the comparison includes comparison of the 3D model to the postoperative image data.

11. A method for generating a preoperative plan for an orthopedic surgical procedure, the method comprising:
retrieving, from a database; generalized data of previous bone models generated for orthopedic surgical procedures and surgical outcome information for the orthopedic surgical procedure;
retrieving, from the database, patient-specific information related to the orthopedic surgical procedure, including range of motion data;
automatically generating the preoperative plan for the orthopedic surgical procedure using the generalized data, the surgical outcome information, and the patient-specific information related to the orthopedic surgical procedure, the generating the preoperative plan including:
selecting, automatically using a processor, an implant based on the range of motion data;
generating, using the processor, a patient-specific 3D model based on the patient-specific information and the generalized data of previous bone models; and
rendering a visual depiction of the implant with the patient-specific 3D model; and outputting the preoperative plan for display on a user interface,
receiving postoperative image data; and
generating a postoperative outcome study report including a comparison of the preoperative plan with the postoperative image data, wherein the comparison includes comparison of the 3D model to the postoperative image data, and wherein the outcome information includes range of motion data.

12. The method of claim 11, wherein retrieving the surgical outcome information includes retrieving range of motion data.

13. The method of claim 11, wherein retrieving the patient-specific information includes retrieving an image of the patient.

14. The method of claim 11, further comprising outputting a data file including instrumentation to be included with a surgical kit based on the preoperative plan.

15. The method of claim 11, wherein the user interface is presented on a heads-up display.

16. The method of claim 11, wherein the patient-specific information includes data generated or captured during a previous orthopedic surgical procedure for the patient.

17. The method of claim 11, wherein the orthopedic surgical procedure is a knee arthroplasty, and further comprising:
obtaining knee kinematic data intraoperatively;
analyzing the knee kinematic data; and
providing real-time feedback via the user interface based on the analyzed knee kinematic data.

18. The method of claim 17, wherein the feedback includes a validation of implant positioning or an analysis of kinematic data as compared to predetermined data or a threshold.

19. The method of claim 11, further comprising scanning a machine readable code on a surgical kit, an instrument, or an implant selected based on the preoperative plan, and wherein the preoperative plan is automatically output for display on the user interface in response to scanning the machine readable code.

20. At least one machine readable medium including instructions for generating a preoperative plan for an orthopedic surgical procedure, which when executed by one or more processors, cause the one or more processors to:
retrieve; from a database, generalized data of previous bone models generated for orthopedic surgical procedures and surgical outcome information for the orthopedic surgical procedure;
retrieve, from the database; patient-specific information related to the orthopedic surgical procedure, including range of motion data;
automatically generate the preoperative plan for the orthopedic surgical procedure using the generalized data, the surgical outcome information, and the patient-specific information related to the orthopedic surgical procedure, operations to generate the preoperative plan include:
select, via the one or more processors, an implant based on the range of motion data;
generate a patient-specific 3D model based on the patient-specific information and the generalized data of previous bone models; and
render a visual depiction of the implant with the patient-specific 3D model; and
output the preoperative plan for display on a user interface,
receive postoperative image data; and generate a postoperative outcome study report including a comparison of the preoperative plan with the postoperative image data, wherein the comparison includes comparison of the 3D model to the postoperative image data, and wherein the outcome information includes range of motion data.

21. The at least one machine readable medium of claim 20, wherein the outcome information includes range of motion data.

* * * * *